(12) United States Patent
Nakazato

(10) Patent No.: US 8,389,213 B2
(45) Date of Patent: Mar. 5, 2013

(54) METHOD FOR CONCENTRATION OF GENE

(75) Inventor: Hiroshi Nakazato, Yachimata (JP)

(73) Assignee: Suntory Holdings Limited, Osaka (JP)

( * ) Notice: Subject to any disclaimer, the term of this patent is extended or adjusted under 35 U.S.C. 154(b) by 781 days.

(21) Appl. No.: 10/450,905

(22) PCT Filed: Dec. 18, 2001

(86) PCT No.: PCT/JP01/11113
§ 371 (c)(1), (2), (4) Date: Jun. 19, 2003

(87) PCT Pub. No.: WO02/50268
PCT Pub. Date: Jun. 27, 2002

(65) Prior Publication Data
US 2004/0058360 A1    Mar. 25, 2004

(30) Foreign Application Priority Data
Dec. 19, 2000   (JP) ................................. 2000-386025

(51) Int. Cl.
*C12Q 1/68* (2006.01)
(52) U.S. Cl. ........................................ 435/6.1; 435/6.11
(58) Field of Classification Search .................. None
See application file for complete search history.

(56) References Cited

U.S. PATENT DOCUMENTS

| | | | |
|---|---|---|---|
| 5,565,340 A * | 10/1996 | Chenchik et al. ............ | 435/91.2 |
| 6,001,574 A * | 12/1999 | Short et al. .................... | 435/6.18 |
| 6,060,245 A * | 5/2000 | Sorge et al. ........................ | 435/6 |
| 6,455,255 B1 * | 9/2002 | Birkenmeyer et al. ........... | 435/6 |
| 6,500,616 B1 * | 12/2002 | Cullis et al. ........................ | 435/6 |

FOREIGN PATENT DOCUMENTS

| | | |
|---|---|---|
| EP | 959141 | 11/1999 |
| JP | 2000-325080 | 11/2000 |

OTHER PUBLICATIONS

Wieland et al. (1990) A method for difference cloning: Gene amplification following subtractive hybridization. Proceedings of the National Academy of Sciences, USA. vol. 87, pp. 2720-2724.*
Lisitsyn et al. (1993) Cloning the differences between two complex genomes. Science. vol. 259: 946-951.*
Meszaros et al. (1996) Subtractive hybridization strategy using paramagnetic Oligo(dT) beads and PCR. Biotechniques. vol. 20.*
Wieland et al. (1992) Isolation of DNA sequences deleted in lung cancer by genomic difference cloning. PNAS. vol. 89: 9705-9709.*
Duguid et al. (1988) Isolation of cDNAs of scrapie-modulated RNAs by subtractive hybridization of a cDNA library. PNAS. vol. 85: 5738-5742.*
Ko (1990) An equalized cDNA library by the reassociation of short double-stranded cDNAs. Nucleic Acids Research. vol. 18: 5705-5711.*
Chassin et al. Identification of genes overexpressed in tumors through preferential expression screening in trophoblasts. Cancer Research. (1994) 54: 5217-5223.*
Chu et al. Expressed genes in interleukin-4 treated B-cells identified by cDNA representational difference analysis. Molecular Immunology. (1998) 35: 487-502.*
Kotani et al. Sse8387I, a new type-II restriction endonuclease that recognizes the octanucleotide sequence 5'-CCTGCAGG-3'. Nucleic Acids Research. (1990) 18(19): 5637-5640.*
Sagerstrom et al. Subtractive cloning: Past, present, and future. Annual Review of Biochemistry. (1997) 66: 751-783.*
Wenzl et al. Isolation of rare cDNAs by asymmetric self-hybridization. Analytical Biochemistry 2000; 286: 303-305.*
Suzuki et al. Efficient isolation of differentially expressed genes by means of a newly established method, 'ESD'. Nucleic Acids Research (1996) 24(4): 797-799.*
Thorstenson et al. Genome Research (1998) 8: 848-855.*
Cho Tae-Ju et al: "A simulation of subtractive hybridization" Nucleic Acids Research, vol. 26, No. 6, Mar. 15, 1998, pp. 1440-1448, XP002276762. ISSN: 0305-1048.
Milner Joel J et al: "A kinetic model for subtractive hybridization" Nucleic Acids Research, vol. 23, No. 1, 1995, pp. 176-187, XP002276763. ISSN:0305-1048.
Wieland I. et al., A method for difference cloning: gene amplification following subtractive hybridization. Proc Natl Acad Sci USA, Apr. 1990, 87(7), p. 2720-4.
Ko M.S. et al., An' equalized cDNA library' by the reassociation of short double-stranded cDNAs. Nucleic Acids Res, Oct. 11, 1990, 18(19), p. 5705-11.
Diatchenko L., Suppression subtractive hybridization: a method for generating differentially regulated or tissue-specific cDNA probes and libraries. Proc Natl Acad Sci USA, Jun. 11, 1996, 93(12), p. 6025-30.
Diatchenko et al., "Suppression subtractive hybridization: a versatile method for identifying differentially expressed genes", *Methods in Enzymology*, vol. 303, pp. 349-380, 1999.

* cited by examiner

*Primary Examiner* — Angela M Bertagna
(74) *Attorney, Agent, or Firm* — Wenderoth, Lind & Ponack, L.L.P.

(57) ABSTRACT

The present invention provides a method where it is possible to concentrate the gene which is expressed only in small amount from a mixture of the gene being expressed in large amount and the gene being expressed only in small amount even when the gene being expressed in large amount is unknown.

10 Claims, 5 Drawing Sheets

1 2 3 4 5 6 7 8 9 10 11

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial sequence
<220> FEATURE:
<223> OTHER INFORMATION: Ef

<400> SEQUENCE: 1
tccgaaagat aacacctg                                                 18

<210> SEQ ID NO 2
<211> LENGTH: 17
<212> TYPE: DNA
<213> ORGANISM: Artificial sequence
<220> FEATURE:
<223> OTHER INFORMATION: Er

<400> SEQUENCE: 2
gggatacctt tggagat                                                  17

<210> SEQ ID NO 3
<211> LENGTH: 18
<212> TYPE: DNA
<213> ORGANISM: Artificial sequence
<220> FEATURE:
<223> OTHER INFORMATION: Bf
```

-continued

```
<400> SEQUENCE: 3
atttagtgca ggctggaa                                              18

<210> SEQ ID NO 4
<211> LENGTH: 23
<212> TYPE: DNA
<213> ORGANISM: Artificial sequence
<220> FEATURE:
<223> OTHER INFORMATION: Br

<400> SEQUENCE: 4
cgtttcatac attttcccca ttg                                        23

<210> SEQ ID NO 5
<211> LENGTH: 30
<212> TYPE: DNA
<213> ORGANISM: Artificial sequence
<220> FEATURE:
<223> OTHER INFORMATION: Hf

<400> SEQUENCE: 5 acttttgaa aattttatct taatatgtgg                                  30

<210> SEQ ID NO 6
<211> LENGTH: 27
<212> TYPE: DNA
<213> ORGANISM: Artificial sequence
<220> FEATURE:
<223> OTHER INFORMATION: Hr

<400> SEQUENCE: 6
tggccgtcaa tgtatttctt tattaag                                    27

<210> SEQ ID NO 7
<211> LENGTH: 18
<212> TYPE: DNA
<213> ORGANISM: Artificial sequence
<220> FEATURE:
<223> OTHER INFORMATION: Ef2

<400> SEQUENCE: 7
tccgaaagat aacacctg                                              18

<210> SEQ ID NO 8
<211> LENGTH: 17
<212> TYPE: DNA
<213> ORGANISM: Artificial sequence
<220> FEATURE:
<223> OTHER INFORMATION: Er2

<400> SEQUENCE: 8 gggataccttt tggagat                                              17

<210> SEQ ID NO 9
<211> LENGTH: 21
<212> TYPE: DNA
<213> ORGANISM: Artificial sequence
<220> FEATURE:
<223> OTHER INFORMATION: Sf

<400> SEQUENCE: 9
atgcccctag atcctcgaat c                                          21

<210> SEQ ID NO 10
<211> LENGTH: 24
<212> TYPE: DNA
```

```
<213> ORGANISM: Artificial sequence
<220> FEATURE:
<223> OTHER INFORMATION: Sr

<400> SEQUENCE: 10
tcaactttta tcataaaatg tacg                                              24
```

METHOD FOR CONCENTRATION OF GENE

This application is a U.S. National Stage of International Application No. PCT/JP01/11113 filed Dec. 18, 2001.

TECHNICAL FIELD

The present invention relates to a method for concentration of rare gene derived from minor microbes in DNA samples prepared from microbe mixture or derived from microbes which are unable to be cultured or for concentration of rare gene which is expressed in animal and plant cells only in small amount, to rare gene obtained by the said concentrating method, to a method for analysis of the said rare gene, to an apparatus for concentration of the rare gene and to a kit for concentration of the rare gene.

In the present specification, gene which was initially present only in small amount in the DNA sample is referred to as "rare gene" while gene which was initially present in large amount therein is referred to as "abundant gene".

BACKGROUND ART

Useful substances produced by microbes have been widely used as industrial enzymes, antibiotics, etc. while 95-99% of the microbes present in the natural world are unable to be cultured and such microbes where culture is impossible have not been industrially utilized yet. However, useful substances such as novel industrial enzymes and antibiotics can be produced in large quantities if gene of industrially useful enzymes is obtained from microbes which are unable to be cultured or if biosynthetic gene of useful substances such as antibiotics produced by microbes and the said gene can be expressed in an appropriate host. Therefore, its usefulness in industry is quite significant.

Preparation of the above-mentioned useful gene from microbes usually starts from the procedure where the microbe having useful gene is isolated and cultured to extract DNA from the said microbe whereupon a gene library is prepared. Principally, the said gene library is introduced and expressed in an appropriate host and an active transformant is screened and selected by an appropriate method. However, in such a method, much time and labor are needed for the preparation of useful gene from the microbe which occupies only a part of a specimen where various microbes are mixed or from the microbe which is unable to be isolated and cultured. Especially when the amount of the microbe having useful gene in the mixture is small and further when the said microbe is unable to be cultured, preparation of the useful gene from the said microbe is substantially impossible. If the gene derived from the microbe which is present only in little amount in the gene specimen or derived from the microbe which is unable to be cultured in the specimen or, in other words, if the rare gene or the trace gene can be relatively concentrated, screening of the useful gene thereafter becomes efficient whereupon labor, time and cost therefor can be greatly saved.

In the meanwhile, it has been believed that cells constituting the human body are classified into 200 or more types, that each of the cells has common genome having about 100,000 types of genes and that several tens of thousands of genes are expressed depending upon the cell type. Investigation of expression of such gene is becoming more and more important not only for obtaining the information concerning the function of each gene but also for clarifying the life process. In addition, as a result of detailed analysis which has been conducted up to now for small amount of relatively limited gene, it has been found that plural genes act in a cooperative manner in many life processes.

Expression of gene is roughly classified into three classes according to the expressed amount. They are an abundant class of about $10^{3-4}$ copies per cell, an intermediate class of about $10^2$ copies and a rare class of only about $10^1$ copies. On the other hand, with regard to the type of the expressed gene, there are as many as several tens of thousands types per cell in mammals and most of the genes belong to the rare class. Thus, with regard to expressed gene in the cell, there are only few types of gene of an abundant class having many expressed amount ($10^{3-4}$ copies) and there are quite a many types of gene of a rare class having only a little expression ($10^1$ copies) (e.g., Alberts, B., et al. (1989) Molecular Biology of the Cell, 2nd Edition, Garland Publishing Inc.). Under such circumstances, there has been a necessity for an art where many types of genes including rare gene is analyzed in more detail and, as a result of conducting such an analysis, its utilization in a medical field such as genetic diagnosis has been expected.

With regard to the analysis of rare gene at present, there has been known, for example, a method where a multiplex PCR is a base including a canonizing method (Minoru S. H. Ko (1990) *Nucleic Acids Res.*, 18, 5705-5711), a differential display method (Liang, P., and Pardee, A. B. (1992), *Science*, 257, 967-971) and a molecular index method (Kikuya Kato (1995), *Nucleic Acids Res.*, 23, 3685-3690, etc.) and also a method using DNA chips. In a canonizing method, a high-molecular nucleic acid mixture is placed under a hybridization condition and, after an appropriate period, nucleic acid becoming a double-stranded state is separated from that remaining in a single-stranded state whereupon the rare gene can be concentrated to the amount of the same degree as the abundant gene. In a canonizing method however, it does not happen that, after the treatment, numbers of rare gene are more than those of abundant gene and, therefore, the effect of concentration is limitative. In case an analysis using a multiplex PCR such as a differential display method is carried out, it has been known that a competitive PCR takes place and a strong bias is applied to the existing amount of the gene whereby the detecting sensitivity lowers as compared with the common PCR and accordingly that detection of gene of the rare class becomes difficult (David, J. Bertioli, et al. (1995) *Nucleic Acids Res.*, 23, 4520-4523). As a method for overcoming such disadvantages, there is disclosed a method in Japanese Patent Laid-Open No. 2000/37,193 where known gene which is abundantly present in a nucleic acid sample is removed and rare gene is concentrated. However, such a method is not applicable unless the gene which is abundantly present is a known one.

On the other hand, the so-called subtraction method and modified methods thereof are available for the identification of mutant gene of some organism species (Ellen E. Lamer and E. Palmer (1984), *Cell*, 37, 171-177; Ilse Wieland, et al. (1990) *Proc. Natl. Acad. Sci. USA*, 87, 2720-2724; Anne Kallioniemi, et al. (1992) *Science*, 258, 818-821; and Nikolai Lisitsyn, et al. (1993) *Science*, 259, 946-951). They are the methods where, between the genes (say, A and B) in which most of them are the same in two individuals of the same organism species, gene which is different in terms of quality or quantity is concentrated and separated or where, in cDNA prepared from mRNA in the cells of the same type in two different states, genes (say, A and B) having different existing amounts are concentrated and separated. Its principle is that, when the genes in A(B) which are the same as B(A) are removed by genes of B(A) by any means, the specific gene which is present only in A(B) can be prepared. Accordingly, in the said method, two kinds of DNA samples in which most of the genes contained therein are the same are inevitably necessary.

However, in some specimens in the natural world (such as soil, lake water and river water), very many types of microbes are present and it is usual that the microbe composition varies for each specimen where each has its inherent composition. Accordingly, when rare gene derived from minor microbe therein is concentrated, it is impossible to prepare two kinds of DNA samples in which most of the genes contained therein—that which subtracts and is subtracted—are the same whereby concentration of the said rare gene using the above-mentioned subtraction method is not possible. Since rare gene in the cDNA sample is concentrated, it is also very difficult to prepare two kinds of cDNA samples wherein one cDNA sample contains the said rare gene and another does not contain the said rare gene where most of genes contained therein are the same. Consequently, it is difficult to concentrate the said rare gene by the above-mentioned subtraction method.

DISCLOSURE OF THE INVENTION

An object of the present invention is to provide a method for concentration of rare gene derived from minor microbes which are present only a little in a specimen or derived from a microbe which is unable to be cultured; to a method whereby rare gene is able to be concentrated from many types of genes expressed in organism bodies, organism tissues or cells even when abundant gene is unknown; and an apparatus and a kit for the concentration of the said rare gene.

The present inventors have repeated intensive studies and, as a result, they have thought of that, in a Cot analysis used for analysis of genome size and analysis of repetitive sequence, reaction rate for re-formation of a double strand is reversely proportional to genome size and is proportional to the concentration of the same sequence whereby rare gene in a DNA sample containing rare gene and abundant gene can be concentrated and have confirmed that rare gene can be concentrated from a mixed solution of *Escherichia coli* DNA, *Bacillus pumilus* DNA and calf thymus DNA whereupon the present invention has been accomplished.

Thus, the present invention relates to the followings.

(1) A method for the concentration of gene which is present in small amount, characterized in that, a DNA sample containing gene which is present in small amount and gene which is present in large amount is subjected to the following operations so that the gene being present in small amount is separated from the gene being present in large amount.

(a) The DNA sample is divided into two equal parts. One DNA sample is called a driver DNA fraction while another DNA sample is called a target DNA fraction;

(b) The target DNA and the driver DNA are mixed and the DNA in the mixed solution is made single-stranded. Alternatively, the target DNA and the driver DNA are made single-stranded and then mixed;

(c) Hybridization is carried out and double stranded DNA formed by the driver DNA and the target DNA is removed from the above-mentioned mixed solution; and (d) The operations of (b) and (c) are carried out once or more times where, instead of the target DNA, there is used a DNA solution obtained in (c) wherefrom the double stranded DNA is removed.

(2) A method for the concentration of gene which is present in small amount, characterized in that, a DNA sample containing gene which is present in small amount and gene which is present in large amount is subjected to the following operations so that the gene being present in small amount is separated from the gene being present in large amount.

(a) The DNA sample is divided into two equal parts. One DNA sample is called a driver DNA fraction while another DNA sample is called a target DNA fraction;

(b) DNA fraction is cleaved in each of the driver DNA fraction and the target DNA fraction. At that time, molecular weight of the driver DNA is made lower than the molecular weight of the target DNA;

(c) The driver DNA is labeled. If desired, a linker adaptor is adhered to the target DNA;

(d) The target DNA is mixed with an excessive amount of the labeled driver DNA, then the DNA in the mixed solution is made single-stranded and a hybridization is carried out;

(e) By means of a labeling of the driver DNA, a double stranded DNA formed by the driver DNA and the target DNA is removed from the above mixed solution; and (f) the operations of (d) and (e) are carried out once or more times, where, instead of the target DNA, there is used a DNA solution obtained in (e) wherefrom the double stranded DNA is removed.

(3) The method for the concentration of gene which is present in small amount according to the above (1) or (2), wherein the ratio (d/t) of the mixed amount (d) of the driver DNA to the mixed amount (t) of the target DNA is more than 1 and up to 1,000.

(4) The method for the concentration of gene which is present in small amount according to the above (2) or (3), wherein the driver DNA is labeled with biotin, digoxin, fluorescein or rhodamine.

(5) The method for the concentration of gene which is present in small amount according to the above (2) to (4), wherein the average chain length of the driver DNA is 200-300 base pairs and the average chain length of the target DNA is 1000 or more base pairs.

(6) The method for the concentration of gene which is present in small amount according to the above (2) to (5), wherein cleavage of DNA is carried out by a four-base recognizing restriction enzyme for the driver DNA fraction while it is carried out by a 5-8-base recognizing restriction enzyme for the target DNA fraction. (7) The method for the concentration of gene which is present in small amount according to the above (6), wherein cleavage of DNA is carried out by MspI for the driver DNA fraction while it is carried out by Sse8387I for the target DNA fraction.

(8) The method for the concentration of gene which is present in small amount according to the above (2) to (5), wherein cleavage of DNA is carried out by ultrasonic wave or mechanical shearing force.

(9) A method for the concentration of gene which is present in small amount, characterized in that, a DNA sample containing gene which is present in small amount and gene which is present in large amount is subjected to the following operations so that the gene being present in small amount is separated from the gene being present in large amount.

(a) The DNA sample is divided into two. One DNA sample is called a driver DNA fraction while another DNA sample is called a target DNA fraction;

(b) DNA is cleaved in each of the driver DNA fraction and the target DNA fraction. At that time, molecular weight of the driver DNA is made lower than that of the target DNA. If desired, a linker adaptor is adhered to the target DNA;

(c) DNA is made single-stranded in each of the driver DNA fraction and the target DNA fraction;

(d) The driver DNA which is made single-stranded as such is fixed on a carrier;

(e) The carrier where the single stranded driver DNA is fixed is contacted or mixed with a solution of the target DNA made into single-stranded to carry out a hybridization;

(f) The carrier and the solution are separated and the target DNA forming a double stand with the driver DNA is removed; and (g) The operations of (e) and (f) are carried out once or more times using a target DNA solution obtained in (f) instead of the target DNA solution.

(10) The method for the concentration of gene which is present in small amount according to the above (1) to (9), wherein the DNA sample is a DNA sample which is prepared from a specimen where at least two kinds of microbes, organism bodies, organism tissues or cells are mixed or is a nucleic acid extracted from organism individuals, organisms tissue or cells and/or a DNA sample prepared from the said nucleic acid.

(11) A DNA sample which is prepared by the method mentioned in the above (1) to (10), characterized in that, the existing ratio of the rare gene having small existing amount before the treatment to the gene having much existing amount before the treatment increases after the treatment.

(12) A method for the analysis of rare gene which is characterized in comprising a step where the gene existing in small amount (hereinafter, referred to as "rare gene") is concentrated by the method mentioned in the above (1) to (10), a step where the rare gene is obtained from the resulting DNA sample where the rare gene is concentrated and the step where base sequence of the rare gene is analyzed.

(13) A gene obtained from the DNA sample obtained by the method mentioned in the above (1) to (10)where the gene being present in small amount is concentrated.

(14) An apparatus for the concentration of rare gene which is characterized in comprising (a) a means where DNA in a mixed solution of the target DNA and the labeled driver DNA is made into single-stranded, (b) a means where hybridization is carried out, (c) a means where double stranded DNA formed by the driver DNA and the target DNA is removed by means of labeling of the driver DNA and (d) a means where the DNA solution obtained by (c) wherefrom double stranded DNA is removed is used instead of the target DNA and the operations of (b) and (c) are repeated.

(15) An apparatus for the concentration of rare gene which is characterized in comprising (a) a means where the driver DNA made into single-stranded is fixed to a carrier, (b) a means where the carrier to which the single stranded driver DNA is fixed is contacted to or mixed with a solution of the target DNA made single-stranded to carry out a hybridization, (c) a means where the carrier and the solution are separated so as to remove the target DNA forming a double strand with the driver DNA and (d) a means where the operations of (b) and (c) are repeated using the target DNA solution obtained in (c) instead of the target DNA solution.

(16) A kit for the concentration of rare gene which is characterized in comprising a means for cleaving the DNA, a labeled substance or carrier, a reagent for labeling the DNA or for fixing the DNA to the carrier, a reagent for hybridization and a means for removing a double stranded DNA of the driver DNA with the target DNA.

BEST MODE FOR CARRYING OUT THE INVENTION

The present invention will now be illustrated in detail as hereunder. Firstly, there will be mentioned a Cot analysis (Koji Sawada, et al.: *Shin Seikagaku Jikken Koza, Kakusan I*, Chapter 10, Fractionation of Nucleic Acid by Hybridization, pages 193-238) which was a theoretical background of the present invention.

Hybrid formation reaction of a high-molecular nucleic acid follows the following reaction formula of the second order where an effective collision among complementary chains is a rate-determining factor and the reaction rate is proportional to a square of the concentration [C] of single stranded DNA.

$$d[C]/dt = -k[C]^2 \quad (1)$$

(in the formula, [C] is concentration of the single stranded DNA, t is reaction time and k is reaction rate constant)

When repetitive sequence is contained as in the case of DNA of animal cells, the initial concentration is different for each sequence and, therefore, progress of the reaction is a multi-phase type. When one of the complementary chains is in a great excess (20-fold or more), it is possible to treat as a reaction of the pseudo-first order.

Using a kinetic consideration in hybridization reaction of nucleic acid in liquid phase, the primary structure of nucleic acid can be analyzed. That is Cot and Crt analyses. Cot analysis is an analysis of DNA-DNA hybridization while Crt analysis is an analysis of DNA-RNA or RNA-RNA hybridization and the latter is called Rot analysis as well. In 1968, Britten and Kohne kinetically analyzed the re-formation reaction of double stranded DNA of animal cell DNA and firstly shown that Cot analysis was able to be utilized for (1) analysis of genome size (multiplicity of base sequence of genomic DNA) and for (2) analysis of repetition of base sequence (R. J. Britten and D. E. Kohne, *Science*, 161, 529). Cot and Crt analyses are also used as indexes for fractionation of nucleic acid.

(1) Cot analysis and genome size

When the formula (1) is integrated and the initial concentration is $[C_0]$, $$[C]/[C_0] = 1/(1+k[C_0]t) \quad (2)$$

Figure 1:
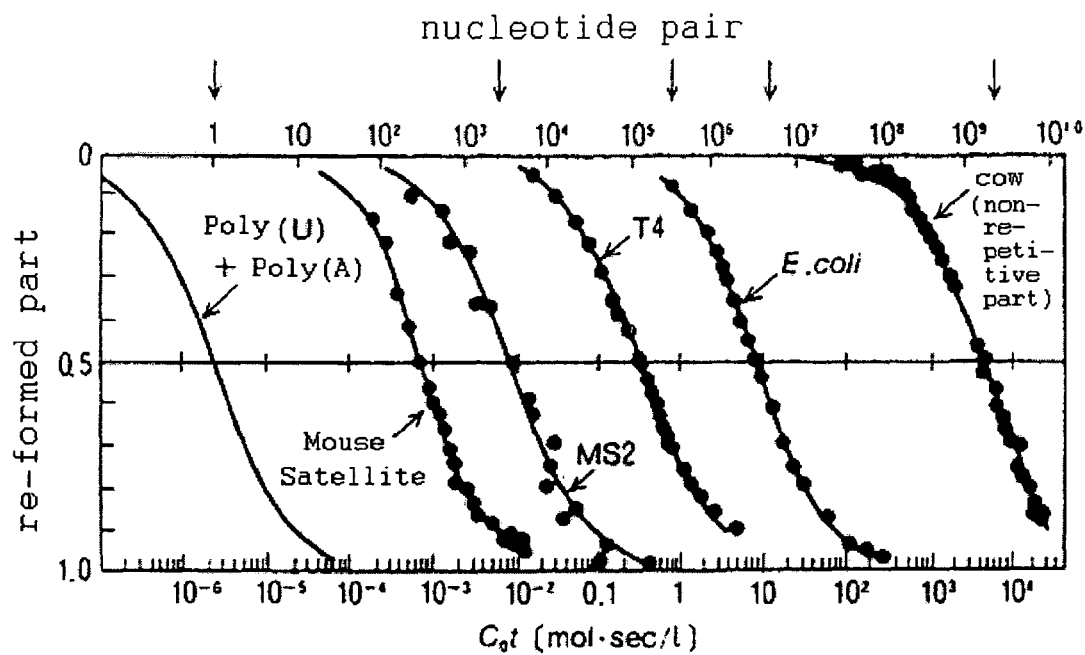
FIG. 1 shows the relation between genome size and $Cot_{1/2}$. To be more specific, it shows re-formation of various double stranded nucleic acids. The genome size is shown on the upper part of the drawing in terms of the ratio to nucleotide pairs (*Shin Seikagaku Jikken Koza, Kakusan I*, page 200).

(in the formula, $[C_0]$ is the initial concentration of single stranded DNA and t and k have the same meanings as defined above) is established and, when $[C_0]t$ is plotted on the abscissa while $[C]/[C_0]$ is plotted on the ordinate, a Cot curve is obtained (FIG. 1).

As to the unit of Cot, nucleotide mol.sec/liter is used. When average molecular weight of the nucleotide is 314, 1 μg/ml DNA is $3.19 \times 10^{-6}$ nucleotide mol./liter and, therefore, $$[C_0]t = DNA(\mu g/ml) \times 1.15 \times 10^{-2} \times time(hr) \quad (3).$$

When this is approximated, $$[C_0]t = DNA(A260) \times time(hr)/2 \quad (4)$$

(in the formula, A260 is an absorbance at 260 nm.)

When there is no repetitive sequence in the DNA molecule, the Cot curve becomes a sigmoid curve of the first order (FIG. 1).

From (2), there is established $$([C_0]-[C])/[C] = k[C_0]t \quad (5)$$

(in the formula, $[C_0]$, [C], t and k have the same meanings as defined above) and, when $[C_0]t$ is plotted on the abscissa while $([C_0]-[C])/[C]$ is plotted on the ordinate, a straight line is obtained. Reciprocal of its gradient is $[C_0]t_{1/2}$.

$$[C_0]t_{1/2} = 1/k \quad (6)$$

(in the formula, $t_{1/2}$ shows the time when 50% of the single stranded DNA became the double stranded DNA. $[C_0]$ and k have the same meanings as defined above.)

When DNA concentration is given in terms of the nucleotide mol concentration, the reaction rate for re-formation of the double strand is inversely proportional to genome size and, therefore, it is proportional to $[C_0]t_{1/2}$. From those, genome sizes of various organisms can be calculated (FIG. 1).

(2) Repetitive (Repeated) Sequence

Figure 2:
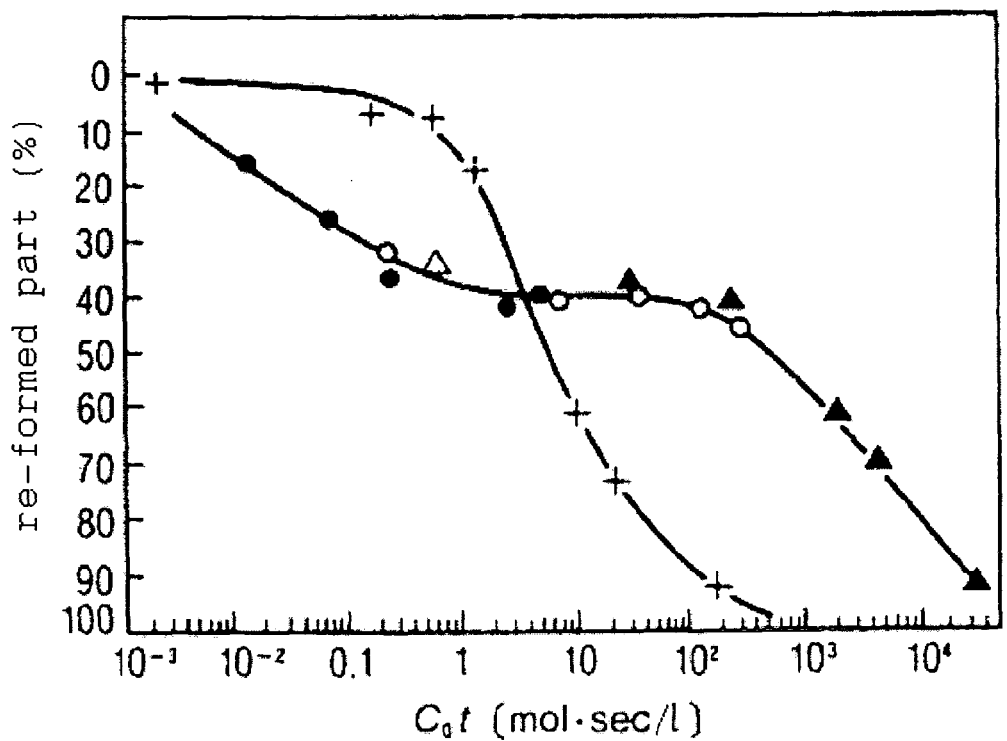
FIG. 2 shows a re-formation of calf thymus DNA. Δ (open triangle) shows a sample where concentration of the calf thymus DNA is 2 μg/ml, ● shows a sample where concentration of the calf thymus DNA is 10 μg/ml, ○ shows a sample where concentration of the calf thymus DNA is 600 μg/ml, ▲ (black triangle) shows a sample where concentration of the calf thymus DNA is 8,600 μg/ml and+ shows a sample where 8,600 μg/ml of calf thymus DNA is added using 43 μg/ml of radio-labeled *Escherichia coli* DNA as an internal standard (*Shin Seikagaku Jikken Koza, Kakusan I*, page 199).

When there are repetitive sequences in the DNA molecule, its Cot curve is a result of synthesis of primary sigmoid curve for a unique sequence and primary sigmoid curve for each repetitive sequence. In the case of calf thymus DNA, the reaction can be divided into two stages and is approximated as a synthesis of primary sigmoid curve in which $[C_0]t_{1/2}$ value is 0.03 for about 40% while, for about 60%, $[C_0]t_{1/2}$ value is 3000. It can be said that the latter is a unique sequence while the former is a highly repetitive sequence having 100,000 copies (FIG. 2). When the reaction is stopped at an appropriate time and the single stranded DNA and the double stranded DNA are separated, it is possible that the unique sequence and the repetitive sequence are separated.

Now, the DNA which is extracted from a specimen such as soil, lake water or river water where at least two kinds of microbes, organism bodies, organism tissues or cells are present in a mixed state can be regarded as equivalent to genome of a higher animal and is defined as metagenome. In the metagenome, gene derived from microbes, etc. in minimum amount can be considered as unique sequence while gene derived from microbes existing in more amounts can be considered as repetitive sequence. The said repetitive sequence is classified into repetitive sequence of high degree, repetitive sequence of medium degree and repetitive sequence of low degrees depending upon the existing numbers.

In addition, in the nucleic acid extracted from organism individuals, organism tissues or cells and/or DNAs prepared from the said nucleic acid, there is also much multiplicity in its existing amount as same as in the case of cDNA prepared from mRNA and classification into unique sequence and repetitive sequence is possible.

According to the above-mentioned theory for Cot analysis, the higher the copy numbers in DNA, the quicker the formation of double strand and, therefore, when a DNA sample used in the present invention is made into single-stranded under an appropriate condition, then double strand is re-formed and the resulting double stranded DNA is separated and removed by an appropriate method, the rare gene is relatively concentrated in the remaining single stranded DNA sample. However, the thing which is to be noted here is that the concentration in that case is just relative and the rare gene never becomes a majority finally but, even in its highest state, the amount is nearly the same at best. As mentioned above, this is a method which is actually used as a canonizing method.

However, it has been thought of that, by the following method, the existing amount of rare gene can be made larger than the abundant gene after the treatment whereupon the present invention has been accomplished.

To be more specific, the method for the concentration of gene according to the present invention is characterized in that a DNA sample containing rare gene and abundant gene is subjected to the following treatments to separate the rare gene from the abundant gene so as to concentrate the rare gene. Thus, (a) the DNA sample is divided into two. One DNA sample is called a driver DNA fraction while another DNA sample is called a target DNA fraction; (b) the target DNA and the driver DNA are mixed and the DNA in the mixed solution is made single-stranded. Alternatively, the target DNA and the driver DNA are made single-stranded and then mixed; (c) hybridization is carried out and double stranded DNA formed by the driver DNA and the target DNA is removed from the above-mentioned mixed solution; and (d) the operations of (b) and (c) are carried out once or more times where, instead of the target DNA, there is used a DNA solution obtained in (c) wherefrom the double stranded DNA is removed.

Its principle will be illustrated as hereunder. Here, abundant gene is called gene A while rare gene is called gene B. Partial sequence of gene A in the driver DNA and/or a specific sequence including the surrounding sequence thereof is called A while partial sequence of gene B therein and/or a specific sequence including the surrounding sequence thereof is called B. With regard to A and B, the same sequence is present in the target DNA fragments as well. $[X^n]$ means the concentration of X when hybridizing and non-hybridizing separation are carried out for n times. "=~" means the same amount or the amount in the same degree.

In the operations of the first hybridization and hybridizing and non-hybridizing separation, A is greatly removed and its concentration becomes [target $A^1$]([target $A^0$]>[target $A^1$]). On the other hand, [target $A^0$+driver $A^0$]>>[target $B^0$+driver $B^0$] and, therefore, when Cot is appropriate, there is almost no change in [target $B^1$]. In the next hybridization, [target $A^1$+driver $A^0$]=~[driver $A^0$]>>[target $B^1$+driver $B^0$] and, therefore, the reaction is a pseudo-first order reaction which only depends upon the concentration of the driver DNA. Thus, as compared with A, hybridization of B can be mostly neglected and, after the hybridizing and non-hybridizing separating operation, target A is further removed to give [target $A^2$]([target $A^1$]>[target $A^2$]) but there is almost no change in [target $B^2$]. When that is repeated, there is a result of [target $A^n$]<<[target $B^n$]=~[target $B^0$] whereupon only gene B having B remains in the target DNA.

Thus, the characteristic feature of the method for the concentration of rare gene according to the present invention is that the driver A freshly supplied for each hybridization is always in a significantly high concentration in the hybridization system and accordingly that the hybridization speed of A is significantly high. When concentrations of A and B become the same degree in the conventional canonizing method, probability of hybridization of each becomes same and, therefore, it is not possible that one of them is further concentrated having priority to another. In accordance with the present invention however, since concentration of the driver A is significantly higher at all times, it is possible to concentrate until gene B becomes more than gene A as shown below.

(i) In case [target A]>>[target B] (in the case of the first operation)

In that case, the driver A is present in large amount in a hybridization system where the target DNA and the driver DNA are mixed and, therefore, the possibility that driver A effectively collides to the target A to hybridize is far higher than the case of B. When the double stranded DNA formed by the driver DNA and the target DNA is selectively removed, the target A can be efficiently removed while the target B is rarely removed but remains in the system. Accordingly, it is possible to separate the gene A (abundant gene) and the gene B (rare gene) so as to concentrate the gene B (rare gene).

(ii) [target A]=~[target B] (when the operation is repeated)

Even repeated concentration is further carried out and "target $A^{m}$" and "target $B^{m}$" become the same degree, concentration of the freshly supplied driver A is significantly more in the new hybridization system where this solution and the driver DNA are mixed and, therefore, possibility of an effective collision of the target A with the driver A is far higher than the probability of an effective collision of the target B with the driver B. Accordingly, the target A which is hybridized with the driver A is removed and most of the target B remains in the system. Therefore, the gene B (rare gene) can be concentrated until its amount becomes more than gene A (abundant gene).

With regard to the DNA sample used in the present invention, there is no particular limitation but anything may be used. An example is a DNA sample which is extracted from a sample where at least two or more kinds of microbes, organisms, organism tissues or cells are mixed. Therefore, it is possible to use DNA extracted from a sample which has an inherent microbe composition obtained from the natural world such as soil, lake water and river water without separation and culture of the microbe. The method for the concentration of minor microbes according to the present invention has such an advantage that it is applicable to a sample having such an intrinsic microbe composition as well.

The DNA sample used in the present invention may be a DNA sample which is nucleic acid extracted from organism individuals, organism tissues or cells and/or a DNA sample prepared from the said nucleic acid. Its examples are tissues where inflamed tissue and normal tissue are mixed; cells or microbes where cancerous cells and normal cells are mixed; and a cDNA sample prepared from mRNA and/or DNA extracted from a mixture of virus-infected cells and non-infected cells. In addition, it may be a cDNA sample which is prepared from mRNA where many kinds of genes are expressed in cells.

With regard to a method for the extraction of DNA, there may be used a method which is known per se such as an alkaline SDS method, a centrifugal method and a combination thereof. It is also possible to appropriately use a commercially available DNA extracting kit.

As an embodiment of the present invention, there may be exemplified a method where (1a) a DNA sample is divided into two (in which one DNA sample is called a driver DNA fraction while another DNA sample is called a target DNA fraction), (1b) the target DNA and the driver DNA are mixed and the DNA in the mixed solution is made single-stranded or, alternatively, the target DNA and the driver DNA are made single-stranded and then mixed, (1c) hybridization is carried out and double stranded DNA formed by the driver DNA and the target DNA is removed from the above-mentioned mixed solution and (1d) the operations of (1b) and (1c) are carried out once or more times where, instead of the target DNA, there is used a DNA solution obtained in (1c) wherefrom the double stranded DNA is removed whereby abundant gene is separated from rare gene and the rare gene is concentrated.

In the above operation (1a), the DNA sample may be freely divided into two. One of the DNA samples is called a driver DNA fraction while another DNA sample is called a target DNA fraction. However, when the DNA sample is available only a little, it is preferred that, taking the mixing ratio of the target DNA and the driver DNA in the operation (1b) into consideration, division into the two is conducted so as to make the amount of the driver DNA fraction more. Further, when the total DNA amount is not sufficient, it is also possible that it is previously amplified by means of a PCR, separated into the target DNA fraction and the driver DNA fraction and subjected to the following operations. When only the driver DNA fraction is amplified by the PCR in that case, difference in the amplified degree depending upon the sequence will give a complicated inclination to the sequence which will be concentrated later.

In the operation (1b), it is preferred to mix an excessive amount of the driver DNA to the target DNA. This is because, when an excessive amount of the driver DNA is added, the abundant gene can be efficiently removed. To be more specific, it is appropriate that the ratio (d/t) of the mixing amount (d) of the driver DNA to the mixing amount (t) of the target DNA is more than 1 but not more than 1000, preferably about 10-1000 or, more preferably, about 100-1000. Especially when the mixing amount of the driver DNA is more, time for the hybridization can be made shorter. Accordingly, in the case where, for example, the DNA sample is not sufficiently available in the present invention, it is still appropriate even if the above-mentioned mixing ratio (d/t) is more than 1 but not more than 10 or, more preferably, about 10.

With regard to a method for making the DNA single-stranded, a method which is known per se may be used and, for example, heat of about 94° C. is applied for about one minute or an alkaline treatment is applied whereby a single stranded product is prepared although the conditions mentioned in the Examples are preferred. Alternately, it is also possible that a single stranded product is prepared after mixing the target DNA and the driver DNA or that, before mixing, each of the target DNA and the driver DNA is made single-stranded.

In the above-mentioned operation (1c), the target DNA and the driver DNA are hybridized. Conditions for the hybridization may be followed a method which is known per se although the conditions mentioned in the Examples are preferred. Here, the hybridization of the target DNA with the driver DNA also includes a state where the driver DNA is hybridized to a part of the target DNA and a state where plural driver DNAs are hybridized to the target DNA.

After that, a double stranded DNA where the target DNA and the driver DNA are hybridized is removed. At the same time, a double stranded DNA where driver DNAs are hybridized and a single stranded DNA may be removed as well. With regard to a method for the removal of a double stranded DNA where the target DNA and the driver DNA are hybridized, a method which is known per se may be used such as, for example, a batch method using hydroxyapatite, a column chromatographic method and a specific gravity centrifugal method using CsCl or the like.

As a result of the above-mentioned operation (1c), the abundant gene is removed and the rare gene is concentrated. It is however preferred that, in order to fully remove the abundant gene, the operations of (1b) and (1c) are carried out using a DNA solution wherefrom a double stranded DNA obtained in (1c) is removed instead of the operation of (1d) where the target DNA is used and it is more preferred to repeatedly carry out at least the operation (1d) once or more times.

Another preferred embodiment of the present invention is a method for the concentration of rare gene by separation of rare gene from abundant gene comprising as follows. Thus, (2a) a DNA sample is divided into two equal parts (where one DNA sample is called a driver DNA fraction while another DNA sample is called a target DNA fraction), (2b) DNA is cleaved in each of the driver DNA fraction and the target DNA fraction so that molecular weight of the driver DNA is made lower than the molecular weight of the target DNA, (2c) the driver DNA is labeled and, if desired, a linker adaptor is adhered to the target DNA, (2d) the target DNA is mixed with an excessive amount of the labeled driver DNA, then the DNA in the mixed solution is made single-stranded and a hybridization is carried out, (2e) by means of a labeling of the driver DNA, a double stranded DNA formed by the driver DNA and the target DNA is removed from the above mixed solution. At that time, a double stranded DNA formed by the driver DNAs and a single stranded driver DNA are also removed. After that, (2f) the operations of (2d) and (2e) are carried out once or more times, where, instead of the target DNA, there is used a DNA solution obtained in (2e) wherefrom the double stranded DNA is removed.

With regard to a method for the cleavage of the DNA in the above-mentioned operation (2b), a method which is known per se may be used such as, for example, treatment with restriction enzyme, treatment with ultrasonic wave and physical shearing force. When the cleavage is carried out using a restriction enzyme, it is possible to cleave into DNA fragments of a desired size by the use of restriction enzymes where the recognizing base pairs are different. For example, when a 8-base recognizing Not I is used, the presumed fragment length is 65,536 base pairs in average corresponding to about 60 genes of the microbe. When a little shorter one is desired, there is used Cpo I recognizing 7 bases and, since one base pair is A or T, a presumed average length is $4^6 \times 2 = 8,192$ base pairs and the resulting length contains 7-8 genes.

Generally, when the target DNA is made larger, a product where genes are connected in plural can be obtained. Accordingly, with regard to the target DNA, that where an average chain length is about 1,000 base pairs or more is preferred. It is frequent that the gene related to a certain metabolic system prepares a gene cluster where the said genes are connected in plural and, therefore, the method according to the present invention is useful for the preparation of cluster gene. At that time, although the size of the diver DNA may be in the same degree as that of the target DNA, it is preferred to be small since efficiency and specificity of the hybridization are enhanced by that. To be more specific, it may be about 200-300 base pairs which is the size (chain length) of the DNA commonly used for carrying out the Cot analysis. When the size (chain length) of DNA is too long, constitution of the sequence on the single stranded DNA becomes complicated in such a manner that, in some parts, there is a similar sequence while, in other parts, there is a unique one. Consequently, the above-mentioned size is preferred.

In order to make the molecular weight of the driver DNA lower than that of the target DNA as such, it is preferred that the cleavage of DNA is carried out in the operation (3a) that restriction enzyme recognizing 4 bases is used for the driver DNA fraction while, for the target DNA fraction, a restriction enzyme recognizing 5-8 bases is used. In the driver DNA fraction, it is more preferred to cleave the DNA by a 4-base-recognizing Msp I for the driver DNA fraction while, for the target DNA fraction, by a 8-base-recognizing Sse8387I.

It is preferred that the driver DNA is previously labeled before the hybridization is carried out (operation (2c)). As a result of the labeling, there is an advantage that a double stranded DNA where the driver DNA and the target DNA are hybridized can be efficiently removed. For the labeling of the driver DNA, anything which is known per se may be used so far as it is able to separate the labeled DNA and the non-labeled DNA. In addition to avidin which is used in the Example, it is also possible to use, for example, digoxin, fluorescein, rhodamine, etc.

In removing the double stranded DNA formed from the driver DNA and the target DNA from the mixed solution (operation (2e), the removal can be carried out by a method which is known per se depending upon the label. When biotin is used as a label for example, Dynabeads to which avidin is bonded is able to remove a double stranded DNA where the target DNA and the driver DNA are hybridized. A method where an anti-labeled antibody is used may be exemplified as well.

It is also possible that, after the target DNA is fragmented, a linker adaptor is added thereto (operation (2c)). As a result thereof, amplification by a PCR and integration into a cloning vector after the concentrating operation can be made easier.

In the meanwhile, with regard to other operations, they are the same as the above-mentioned (1a)-(1d).

Still another preferred embodiment of the present invention is a method for the concentration of rare gene where the rare gene is separated from the abundant gene in such a manner that (3a) the DNA sample is divided into two (where one DNA sample is called a driver DNA fraction while another DNA sample is called a target DNA fraction), (3b) DNA is cleaved in each of the driver DNA fraction and the target DNA fraction so that molecular weight of the driver DNA is made lower than that of the target DNA and, if desired, a linker adaptor is adhered to the target DNA, (3c) DNA is made single-stranded in each of the driver DNA fraction and the target DNA fraction, (3d) the driver DNA which is made single-stranded as such is fixed on a carrier, (3e) the carrier where the single stranded driver DNA is fixed is contacted to or mixed with a solution of the target DNA made into single-stranded to carry out a hybridization, (3f) the carrier and the solution are separated and the target DNA forming a double strand with the driver DNA is removed and (3g) the operations of (3e) and (3f) are carried out once or more times using a target DNA solution obtained in (3f) instead of the target DNA solution.

In order to efficiently remove the double stranded DNA where the driver DNA and the target DNA are hybridized, it is also preferred that the driver DNA is previously fixed to the carrier before the hybridization instead of labeling with the driver DNA (operation (3c)). With regard to a method for fixing the driver DNA to the carrier, a method which is known per se may be used. Its examples are a method where it is adsorbed with nitrocellulose membrane or Nylon membrane and a method where it is physically adsorbed on the surface of glass which is coated with polylysine or on the surface of glass which is treated with silane. Another example is a method where the above driver DNA labeled with biotin is fixed on a carrier where streptavidin is made into a solid phase.

When the driver DNA is fixed to the carrier as such, it is possible that most of a double stranded DNA formed by the driver DNA and the target DNA or, in other words, an abundant gene is easily removed from the solution of the target DNA by separating the carrier and the target DNA solution (operation (3f)).

Figure 6:
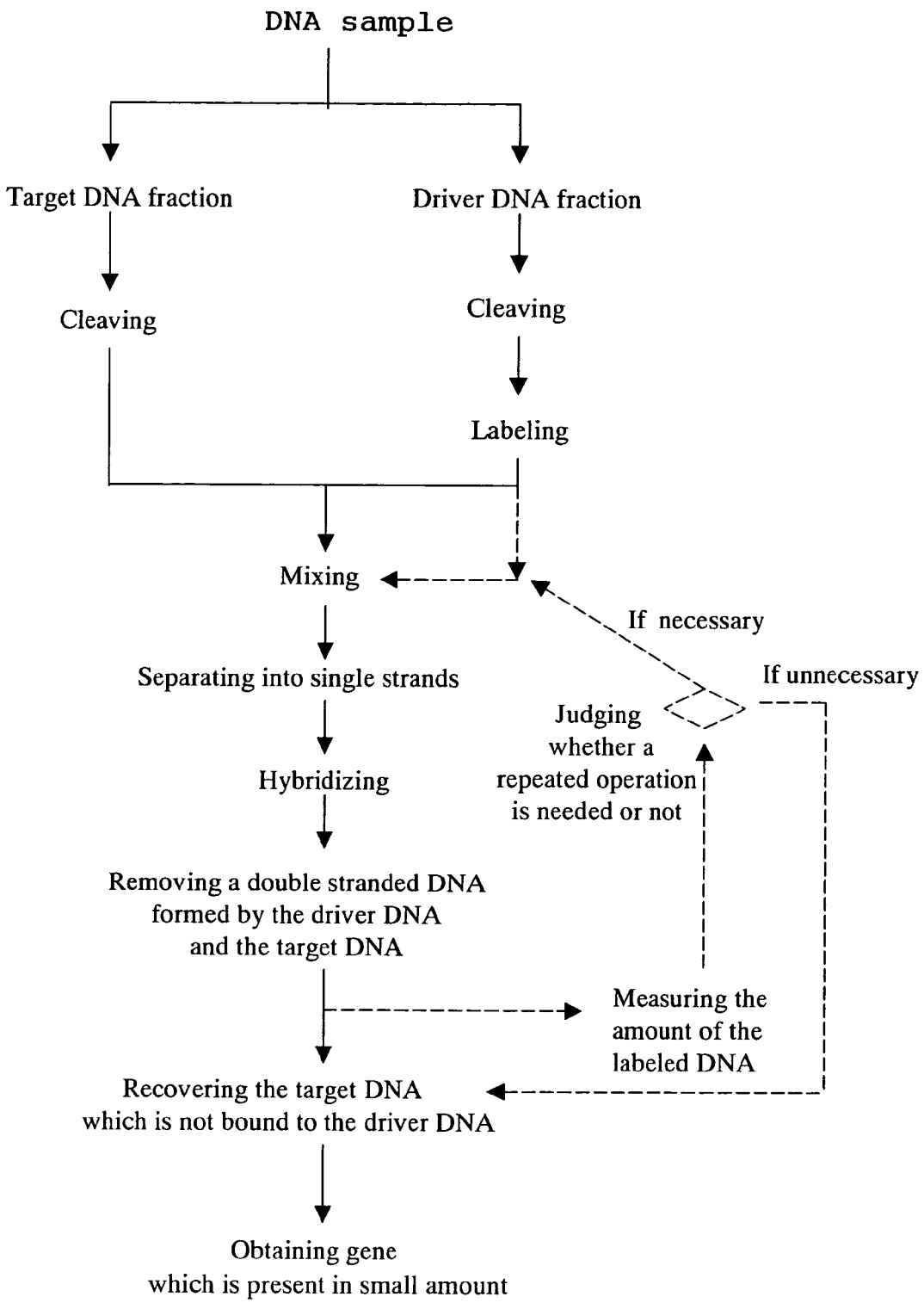
FIG. 6 shows a flow of operations in one embodiment of the method for the concentration of rare gene according to the present invention. Dotted lines show the flow of the operations in the case of identifying the state of removal of abundant gene.

In order to remove the abundant gene with a good precision at this time, it is also effective that removal is carried out together with checking the removing state of the abundant gene. Therefore, in the present invention, it is also possible to use, for example, a method where degree of removal of the abundant gene is monitored using a removed double stranded DNA solution or using a recovered single stranded DNA solution and, if desired, an operation (2f) or (3g) where the remaining abundant gene is removed may be carried out. Such a method may be a combination of a method which is known per se and a specific embodiment is shown in FIG. 6. Until the hybridized double stranded DNA is removed, the same operation as above is carried out. The removed double stranded DNA solution is used and the abundant gene therein is detected by a method which is known per se. When the result is that the abundant gene is not substantially detected or that the said amount is sufficiently decreased as compared with the concentration of the abundant gene in the initially-removed double stranded DNA solution, it means that the abundant gene in the solution is small and, therefore, it is not necessary to further carry out the operation (2f) or (3g) but it is possible to carry out the step for obtaining the rare gene. On the contrary, when the reversed result is obtained, it is preferred to carry out the above-mentioned operation (2f) or (3g).

In order to monitor the degree of presence of removal of such an abundant gene, it is possible to estimate the amount of the abundant gene using a sequence (common sequence) which is common to genomes of organism species existing in large amount as a marker. In order to measure the existing amount of the common sequence, it is possible to utilize a hybridization method where the common sequence is a probe or a PCR where the common sequence is a primer. With regard to the common sequence, a common sequence existing in the gene coding for rRNA (rDNA) is preferred in the case of DNA which is extracted from a specimen where many kinds of organisms are mixed. That is because, since base sequences of rDNA are known for many organism species, it is easy to find out the common sequence for rDNA and further since copy numbers of rDNA per genome are high, the common sequence in rRNA is advantageous as a marker. When organism species existing in large amount are limited such as that they are limited to prokaryotes, there are much more common sequences. When the organism species are further limited such as to actinomyces, there are still more common sequences. There is no need that the common sequence is limited to rDNA but it may be a common sequence in genome of organism species existing in large amount such as a common sequence existing in gene coding for protein which is commonly present in the said organic species. For example, since cytochrome C gene is present in all organism species and its base sequence is known in many of the organism species, the common sequence existing in the cytochrome C gene is appropriate as a marker.

When the abundant gene in the DNA sample is derived from the organism individuals, organisms tissue or cells in the same organism species, the gene which is specific to the said organism species can be used as a marker for estimating the amount of the abundant gene. When the DNA sample is cDNA derived from organism individuals, organism tissues or cells of the same organism species, gene having much expressed amount can be used as a marker.

It is preferred that numbers of repetition of the operations (2f) or (3g) are not decided uniformly but, taking the Cot value into consideration, plural recovered DNA fractions in the DNA fractions which are recovered by the operations for N times are subjected to the preparing operations for the gene. That is because, as a result thereof, there is a possibility of obtaining useful gene from plural DNA fractions having different existing concentrations for each of genes of microbes/organisms where the existing numbers in the first sample are different. As the repetition of the operation goes on, gene in minimum amount can be obtained more easily.

More preferred embodiment of the present invention is a method which will be mentioned as follows. Thus, (4a) the DNA sample is divided into two equal parts (where one DNA sample is called a driver DNA fraction while another DNA sample is called a target) and (4b) a restriction enzyme is used and, in the case of the target DNA fraction, it is cleaved into a long DNA (target DNA) where an average chain length is about 1000 base pairs or more and a short DNA (driver DNA) where an average chain length is about 200-300 base pairs. (4c) The driver DNA is chemically biotinylated. (4d) The said biotinylated driver DNA (its mixing amount: d) and the target DNA (its mixing amount: t) are mixed so as to make their mixing ratio (d/t) more than 1 but not more than 1000 or, preferably about 10 whereby the DNA in the said mixed solution is made single-stranded and the hybridization is carried out in a liquid phase. (4e) Avidin Dynabeads are added to the mixed solution whereby the double stranded DNA formed by hybridization of the driver DNA and the target DNA is removed. Thus, biotin which is adhered to the driver DNA forms a complex with avidin. Therefore, the target DNA hybridized to the driver DNA is trapped by Dynabeads. Since Dynabeads can be easily removed by centrifugal separation, the double stranded DNA formed by hybridization of the driver DNA and the target DNA can be easily removed as well together with Dynabeads. At that time, the double stranded DNA formed by the driver DNAs and the single stranded driver DNA is removed as well. (4f) The operations of (4d) and (4e) are carried out once or more times using the supernatant liquid obtained in (4e) instead of the target DNA.

When the method for the concentration of gene in accordance with present invention as mentioned above is used, there is prepared a DNA sample which is characterized in that the existing ratio of the rare gene before the treatment to the abundant gene increases after the treatment. The rare gene can be prepared from such a DNA sample. In the preparation, there may be used a method which is known per se such as a method described in "Molecular Cloning", 2nd ed., Cold Spring Harbor Laboratory (1989). Commercially available kit may be used as well. When the sequence of the added adaptor linker is used at that time, it is possible to easily clone by a method which is known per se. With regard to the prepared rare gene, its base sequence can be decoded as it is or, after integrating into an appropriate vector and subjecting to subcloning, decoding of the base sequence may be carried out. Decoding of the base sequence may be carried out by a method which is known per se such as that on the principle of a Maxam-Gibert method or a Sangar method or, alternatively, a commercially available DNA sequencer may be used.

The present invention further provides a kit for concentrating the rare gene in the above DNA sample. To be more specific, a kit comprising a means for the cleavage of DNA, a labeling substance or carrier, a reagent for labeling the DNA or a reagent for fixing the DNA to the carrier, a reagent for hybridization and a means for the removal of a double stranded DNA formed by the driver DNA and the target DNA is preferred. Here, the labeled substance or carrier is used for labeling the driver DNA or for fixing the driver DNA so that the double stranded DNA formed by hybridization of the driver DNA and the target DNA is easily removed. Incidentally, "reagent for labeling the DNA" means a reagent which is used for labeling the driver DNA and "a reagent for fixing the DNA to the carrier" means a reagent which is used for fixing the driver DNA. To be more specific, those which are mentioned in the above method for the concentration of the rare gene can be appropriately used. With regard to constitution, form, etc. of the kit, an art which is known per se may be used.

The present invention further provides an apparatus for the concentration of the rare gene in a DNA sample. To be more specific, there is provided an apparatus for the concentration of rare gene which is characterized in comprising (a) a means where DNA in a mixed solution of the target DNA and the labeled driver DNA is made into single-stranded, (b) a means where hybridization is carried out, (c) a means where double stranded DNA formed by the driver DNA and the target DNA is removed by means of labeling of the driver DNA and (d) a means where the DNA solution obtained by (c) wherefrom double stranded DNA is removed is used instead of the target DNA and the operations of (b) and (c) are repeated. Each of the means is as same as the description concerning the above-mentioned method for the concentration of rare gene. Combination of each of the means may be in accordance with a method which is known per se. It is also possible that (a) a means where DNA is cleaved in each of the driver DNA fraction and the target DNA fraction so that the molecular weight of the driver DNA is made lower than that of the target DNA, (b) a means where the driver DNA is labeled or (c) a means where a linker adaptor is attached to the target DNA may be further combined therewith.

Another embodiment of the apparatus for the concentration of the rare gene in a DNA sample according to the present invention is an apparatus for the concentration of rare gene which is characterized in comprising (a) a means where the driver made into single-stranded is fixed to a carrier, (b) a means where the carrier to which the single stranded driver DNA is fixed is contacted or mixed with a solution of the target DNA made into single-stranded to carry out a hybridization, (c) a means where the carrier and the solution are separated so as to remove the target DNA forming a double strand with the driver DNA and (d) a means where the operations of (b) and (c) are repeated using the target DNA solution obtained in (c) instead of the target DNA solution. Each of the means is as same as the description concerning the above-mentioned method for the concentration of rare gene. Combination of each of the means may be done in accordance with a method which is known per se. It is also possible that (a) a means where DNA is cleaved in each of the driver DNA fraction and the target DNA fraction so that the molecular weight of the driver DNA is made lower than that of the target DNA, (b) a means where a linker adaptor is adhered to the target DNA or (c) a means where DNA is made single-stranded in each of the driver DNA fraction and the target DNA fraction.

EXAMPLES

The present invention will now be specifically illustrated by way of the following Examples, but the present invention is not limited thereto.

Example 1

DNA of *Escherichia coli* strain B was purchased from Sigma Co. USA and human genome DNA from Clontech Laboratories Inc., USA. DNA of *Bacillus pumilus* was prepared from the microbe using Gen Torukun (trade name; manufactured by Takara Shuzo).

Incidentally, in the present Examples, the following restriction enzymes, buffers, reagents, etc. were used. Use of each restriction enzyme, reagent, etc. was carried out in accordance with the Directions for Use of the Product.

(a) MspI (manufactured by Takara Shuzo): 10 units/μl [solvents: 10 mM $KPO_4$, 200 mM NaCl, 1 mM EDTA, 1 mM dithiothreitol (DTT), 0.02% bovine serum albumin (hereinafter, referred to as BSA) and 50% glycerol (pH 7.5)]

(b) Sse8387I (manufactured by Takara Shuzo): 10 mM Tris-HCl (pH 7.5), 10 mM $MgCl_2$, 1 mM DTT, 50 mM NaCl and 100 μg/ml BSA (c) TE: 10 mM Tris-HCl, pH 7.5

(d) 10×M: 100 mM Tris-HCl (pH 7.5), 100 mM $MgCl_2$, 10 mM DTT and 500 mM NaCl (e) 10×Mirus Labelling Buffer A (Mirus): 200 mM MOPS, pH 7.5

(f) 20×SSC: 3 M NaCl and 0.3 M $Na_3$-citrate (g) formamide: After addition of AG501-x8, 20-50 mesh, fully regenerated (BioRad Lab., USA), the mixture was mixed by rotating for one night and the resulting supernatant liquid was used.

(h) W×B: 5 mM Tris-HCl, 0.5 mM EDTA and 1 M NaCl (i) DYNABEADS (DYNABEADS M-280 Streptavidin, Japan Dynal K. K. (superparamagnetic monosized polymer particles)): A suspension (1 ml) of DYNABEADS (superparamagnetic monosized polymer particles) was separated into DYNABEADS (superparamagnetic monosized polymer particles) and liquid phase, the DYNABEADS (superparamagnetic monosized polymer particles) was suspended in W×B containing tRNA (20 μg/ml) again and beads and liquid phase were separated by Dynal MPC. That was repeated once again and, finally, DYNABEADS (superparamagnetic monosized polymer particles) was suspended in W×B containing tRNA (20 μg/ml) and the suspension in a necessary amount was placed in each test tube.

[Operation 1. Preparation of DNA mixed solution]

*Escherichia coli* DNA (80 μg) and 8 ng of *Bacillus pumilus* DNA were dissolved in 440 μl of TE to give liquid A.

Human DNA (80 μg), 80 ng of *Escherichia coli* DNA and 0.8 ng of *Bacillus pumilus* DNA were dissolved in 700 μl of TE to give liquid B.

[Operation 2. Preparation of driver DNA (Fragmentation and biotination of DNA)]

To the liquid A containing 75 μg of *Escherichia coli* DNA and 7.5 ng of *Bacillus pumilus* DNA were added 120 μl of 10×B, 600 units of MspI and water to make 1.2 μl, and the mixture was kept at 37° C. for 2 hours to cleave the DNA and then treated at 60° C. for 15 minutes to inactivate the MspI. The reaction solution was divided into three and the DNA fragments were precipitated with ethanol and recovered by treating with a centrifugal separator (hereinafter, they will be referred to as E/B mix DNA fragments).

To the liquid B containing 75 μg of human DNA, 75 ng of Escherichia cdi and 75 ng of *Bacillus pumilus* DNA were added 120 μl of 10×B, 600 units of MspI and water to make 1.2 ml and the mixture was kept at 37° C. for 2 hours to cleave the DNA and then treated at 60° C. for 15 minutes to inactivate the MspI. The reaction solution was divided into three and the DNA fragments were precipitated with ethanol and recovered by treating with a centrifugal separator (hereinafter, they will be referred to as H/E/B mix DNA fragments).

The precipitate in each test tube (each containing ⅓ equivalent of the mix DNA fragments) was dissolved in 200 μl of water and 25 μl of 10×Mirus Labeling Buffer A, then 25 μl of Mirus Label IT reagent were added and the reaction was carried out at 37° C. for 2 hours whereupon the DNA was labeled with biotin. To this were added 25 μl of 5M NaCl and 550 μl of ethanol and the mixture was preserved at −20° C. (hereinafter, the biotinated E/B mix DNA fragments will be referred to as E/B driver DNA and biotinated H/E/B mix fragments will be referred to as H/E/B driver DNA).

[Operation 3. Preparation of target DNA (fragmentation of DNA)]

To the liquid A containing 2.5 μg of *Escherichia coli* DNA and 0.25 ng of *Bacillus pumilus* DNA were added 10 μl of 10×M, 10 μl of 0.1% BSA, 20.4 units of Sse8387I and water to make 100 μl and the mixture was kept at 37° C. for 2 hours to cleave the DNA and treated at 60° C. for 15 minutes to inactivate the Sse8387I. To this were added 20 μg of tRNA, 10 μl of 3M sodium acetate and 220 μl of ethanol and the mixture was preserved at −20° C. (hereinafter, this fragmented DNA is referred to as E/B target DNA).

To the liquid B containing 2.5 μg of human DNA, 2.5 ng of *Escherichia coli* DNA and 0.025 ng of *Bacillus pumilus* DNA were added 10 μl of 10×M, 10 μl of 0.1% BSA, 20.4 units of Sse8387I and water to make 100 μl, and the mixture was kept at 37° C. for 2 hours to cleave the DNA and treated at 60° C. for 15 minutes to inactivate the Sse8387I. To this were added 20 μg of tRNA, 10 μl of 3M sodium acetate and 220 μl of ethanol, and the mixture was preserved at −20° C. (hereinafter, this fragmented DNA will be referred to as H/E/B target DNA).

[Operation 4. Hybridization]

A test tube containing an ethanol-precipitated E/B target DNA was centrifuged at 15,000 rpm for 20 minutes and the supernatant liquid was discarded. To the same test tube were added 400 μl of a suspension of an ethanol-precipitated E/B driver DNA and the mixture was centrifuged at 15,000 rpm for 20 minutes. The supernatant liquid was discarded, 425 μl of a suspension of ethanol-precipitated E/B driver DNA were added, the mixture was centrifuged and the supernatant liquid was discarded. The final precipitate was dissolved in 9.28 μl of water and 0.96 μl of 3N NaOH at room temperature, the mixture was quickly cooled on ice, 0.96 μl of 3N HCl and 50 mM Tris-HCl (pH 7.2) were added thereto and then 8 μl of 20×SSC and 20.8 μl of formamide were added followed by well mixing. One drop of mineral oil was dropped thereinto and the mixture was tightly closed with a cover and kept at 37° C. to carry out a hybridization reaction.

Both H/E/B target DNA and H/E/B driver DNA were similarly treated to carry out a hybridization reaction.

$N^0$ shows a DNA solution where hybrid and non-hybrid operation was carried out for N times.

After 24 hours, 20 μl of the hybridization reaction solution were taken out and added to a test tube in which 1 ml equivalent of DYNABEADS (superparamagnetic monosized polymer particles) suspension was placed. Remainders ($1^0$ and $2^0$) were continued to heat. The said test tube was frequently mixed up for 50 minutes by heating in a constant-temperature bath of 43° C. This was subjected to a Dynal MPC and allowed to stand for several minutes, the liquid phase was divided into two equal parts and each of them was added to two test tubes wherein 1 ml of ethanol cooled at −20° C. was placed, allowed to stand in a freezer of −80° C. for 35 minutes and centrifuged at 15,000 rpm for 20 minutes to obtain a precipitate. The precipitate in one of the test tubes (A) was dissolved in 80 μl water+10 μl of 3N NaOH and the total amount was transferred to another test tube (B) to dissolve the precipitate. On the other hand, ⅓ equivalent of the driver DNA was centrifuged under the same conditions and centrifuged to separate the precipitate, the precipitate was dissolved in 80 μl water+10 μl of 3N NaOH, the test tube (A) was washed with 45 μl thereof and the total amount was washed out into (B). To (B) were added 15 μl of 3N HC1 and 50 mM Tris (pH 7.2), then 300 μl of ethanol of −20° C. were added followed by mixing and the mixture was allowed to stand in a freezer of −80° C. for 30 minutes or longer. To the precipitate obtained by centrifugal separation were added 4.64 μl water+

0.48 μl of 3N NaOH to sufficiently dissolve at room temperature, the solution was quickly cooled on ice, then 0.48 μl of 3N HCl+50 mM Tris-HCl (pH 7.2), 4 μl of 20 ×SSC and 10.4 μl of formamide were added thereto successively, one drop of mineral oil was layered thereon and the mixture was kept at 37° C.

After 20 hours, 40 μl of W×B containing tRNA (20 μg/ml) were added and mixed up, mineral oil was removed as much as possible, chloroform saturated with TE was added and extraction with chloroform was carried out according to a conventional method. The aqueous phase was made 1 ml using W×B containing tRNA (20μg/ml) and added to a test tube in which 1 ml equivalent of washed DYNABEADS (superparamagnetic monosized polymer particles) was placed. This was kept at 43° C. for 50 minutes and, during that period, it was mixed every 1 or 2 minutes. This was then subjected to a Dynal MPC and allowed to stand for several minutes, the liquid phase was divided into two equal parts, each of them was added to a test tube in which 1 ml of ethanol cooled at −20° C. was placed, allowed to stand in a freezer of −80° C. for 35 minutes or longer and centrifuged at 15,000 rpm for 20 minutes to prepare a precipitate. The precipitate was dissolved in each 50 μl of water and 5 μl of 3N NaOH at room temperature and added to the driver DNA precipitate corresponding to one tube, 10 μl of 3N HCl and 50 mM Tris (pH 7.2) were added and then 220 μl of ethanol of −20° C. were added and the mixture was allowed to stand in a freezer of −80° C. for 50 minutes or longer. To the centrifuged precipitate were added 4.64 μl water+0.48μl of 3N NaOH followed by well dissolving at room temperature, the solution was quickly cooled on ice, 0.48 μl of 3N HCl+50 mM Tris-HCl (pH 7.2), 4 μl of 20×SSC and 10.4 μl of formamide were added successively and one drop of mineral oil was layered thereon followed by keeping at 37° C.

After 213 hours and 50 minutes, 10 μl were taken out, 40 μl of W×B containing tRNA (50 μg/ml) were added, mineral oil was removed as mentioned above and the remainder was transferred to a test tube where 500 μl equivalents of washed DYNABEADS (superparamagnetic monosized polymer particles) were placed and rotated and mixed over night at room temperature after attaching to a rotating machine. This was subjected to Dynal MPC to separate a liquid phase, treated with 0.05 ml equivalent of washed DYNABEADS (superparamagnetic monosized polymer particles) and the resulting final liquid phase was subjected to precipitation with ethanol to recover DNA)(3°).

On the other hand, 10 μl were taken out from (1° and 2°) after 119 hours and 5 minutes. The remainder was continued to be warmed. The taken out 10 μl were treated with 0.5 ml equivalent of washed DYNABEADS (superparamagnetic monosized polymer particles) and, as same as above, it was recovered as a precipitate with ethanol together with ⅙equivalent of the driver DNA. To the precipitate were added 9.28 μl water+0.96 μl of 3N NaOH followed by well dissolving at room temperature, the solution was quickly cooled on ice, 0.96 μl of 3N HCl+50 mM Tris-HCl (pH 7.2), 8 μl of 20×SSC and 20.8μl of formamide were successively added thereto and one drop of mineral oil was layered followed by keeping at 37° C. for 87 hours and 10 minutes. After removal of the mineral oil, the liquid phase obtained by the treatment with 1 ml equivalent of washed DYNABEADS (superparamagnetic monosized polymer particles) was further treated with 0.1 ml equivalent of washed DYNABEADS (superparamagnetic monosized polymer particles) and the resulting final liquid phase was precipitated with ethanol to recover nucleic acid)(2°).

The remainder which was kept warming was kept at 37° C. for 289 hours and 20 minutes, similarly treated with 0.5 ml and then with 0.05 ml of washed DYNABEADS (superparamagnetic monosized polymer particles) and the resulting final liquid phase was precipitated with ethanol to recover nucleic acid (1°).

Finally, to all of the precipitates of recovered nucleic acid were added 0.5 μl of ETHACHINMATE and 20 μl of 0.3N NaOH, treated at 37° C. for 1.5 hours to decompose and remove an excessive tRNA, then 20 μl of 0.3 N HCl+5 mM Tris-HCl (pH 7.2) were added and DNA was recovered by precipitating with ethanol followed by dissolving in TE.

Figure 3:
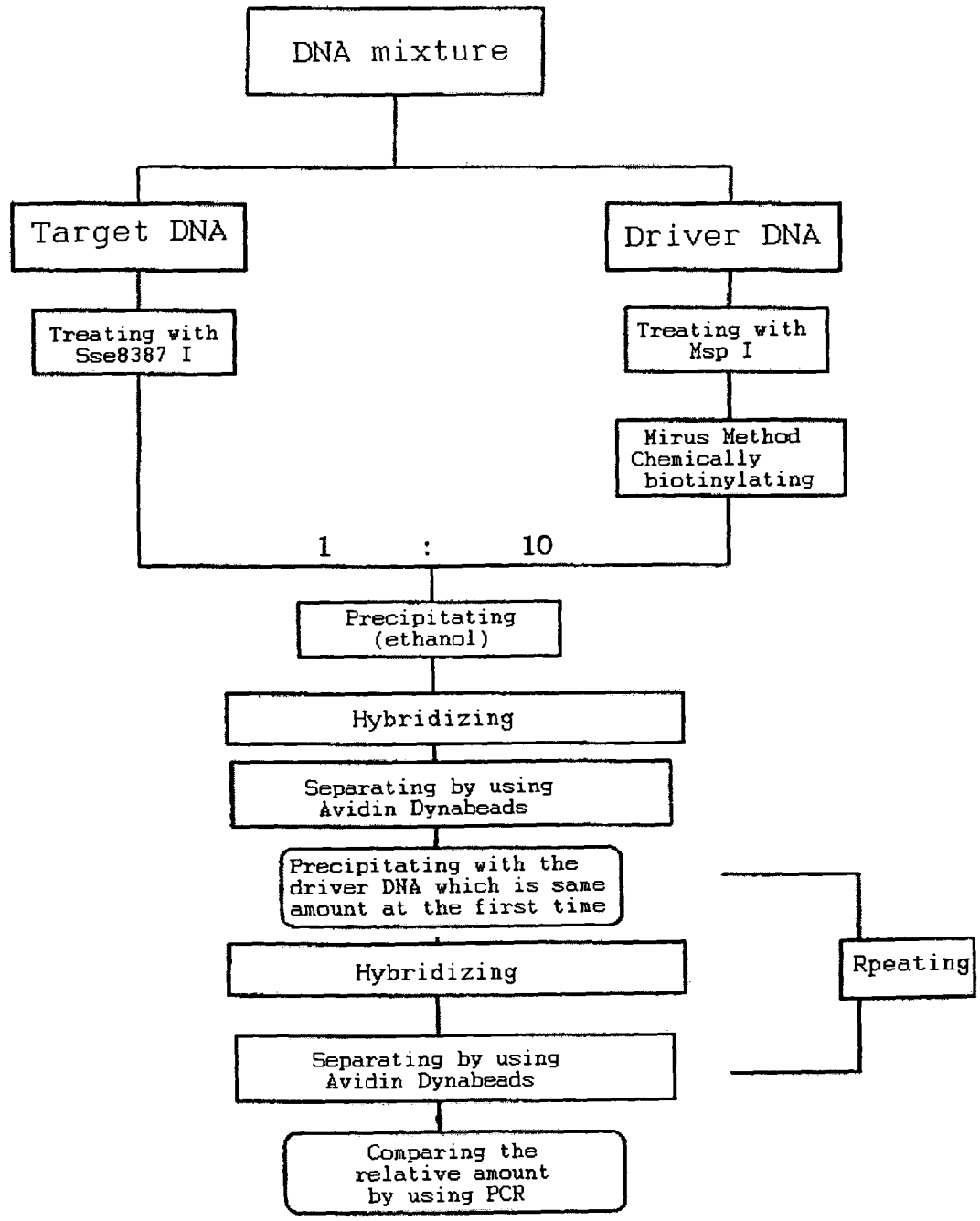
FIG. 3 shows how the operations of the Examples run.

The flow of the above-mentioned experiment is shown by a chart (FIG. 3). Warming time for each fraction and Cot calculated therefrom are summarized in the following table.

TABLE 1

| | | 1° | 2° | 3° |
|---|---|---|---|---|
| Hybridization Time | | 289 h 20 m | 119 h 5 m + 88 h 10 m | 24 h + 20 h + 213 h 50 m |
| Cot | E/B | | | |
| | E. coil | 2,285 | 940 + 316 | 190 + 192 + 1535 |
| | B. pumilus | 0.228 | 0.09 + 0.03 | 0.02 + 0.02 + 0.15 |
| | H/E/B | | | |
| | Human | 2,285 | 940 + 316 | 190 + 192 + 1535 |
| | E. coil | 0.228 | 0.09 + 0.03 | 0.02 + 0.02 + 0.15 |
| | B. pumlius | 0.023 | 0.009 + 0.003 | 0.002 + 0.002 + 0.015 |

Test Example 1

Checking of gene in each nucleic acid fraction

The precipitate was dissolved in TE, an aliguot of the solution was added to prepare 25 μl of PCR reaction solution (comprising 2.5 μl of 10×PCR Buffer, 2 μl of dNTP, 0.25 μl of rTaq, 1 μl of primer set and template DNA and water added to make 25 μl), one drop of mineral oil was added followed by tightly closing, PCR of 94° C./1 minute, 60° C./1 minute and 72° C./2 minutes was carried out for 35 cycles and the mixture was allowed to stand at 72° C. for 8 minutes and cooled down to 23° C. With regard to a primer set, a mixture of each 0.5 μl of Ef and Er (for *Escherichia coli* gene), Bf and Br (for *Bacillus pumilus* gene) or Hf and Hr (for human gene) was used.

Each of the following oligonucleotides was dissolved in TE and the resulting 100 μM solution was used as the above-mentioned primer.

(a) *Escherichia coli*: The following parts of ompA ecompa.gb_bal, 1-2271 CDS 172-669 were used as primers.

```
Ef 1102-1119:
5' TCCGAAAGATAACACCTG 3'        (SEQ ID NO: 1)

Er 1892-1908:
5' GGGATACCTTTGGAGAT 3'         (SEQ ID NO: 2)
```

Amplified product by PCR had 807 base pairs.

(b) *Bacillus pumilus*: The following parts of xynA bpx-yna.gb_bal, 1-1070 CDS 61-747 were used as primers.

```
Bf 243-260:
5' ATTTAGTGCAGGCTGGAA 3'        (SEQ ID NO: 3)

Br 650-672:
5' CGTTTCATACATTTTCCCCATTG 3'   (SEQ ID NO: 4)
```

Amplified product by PCR had 430 base pairs.

(c) Human being: The following parts of IL5h j03478.gb_pr2, 1-3220 were used as primers.

```
Hf 1600-1629:
5' ACTTTTTGAAAATTTTATCTTAATATGTGG 3' (SEQ ID NO: 5)

Hr 1981-2007:
5' TGGCCGTCAATGTATTTCTTTATTAAG 3'    (SEQ ID NO: 6)
```

Amplified product by PCR had 408 base pairs.
The followings were used as other solutions.
(i) 10×PCR Buffer: 100 mM Tris-HCl, pH 8.3+500 mM KCl+15 mM $MgCl_2$
(ii) dNTP mix: each 2.5 mM of dATP+dGTP+dCTP+dTTP
(iii) Taq: 5 units/µl (solvent: 20 mM Tris-HCl+100 mM KCl+0.1 mM EDTA+1 mM DTT+0.5% Tween 20+0.5% Nonidet P-40+50% glycerol)
(iv) DNA template

[Result 1]

Figure 4:
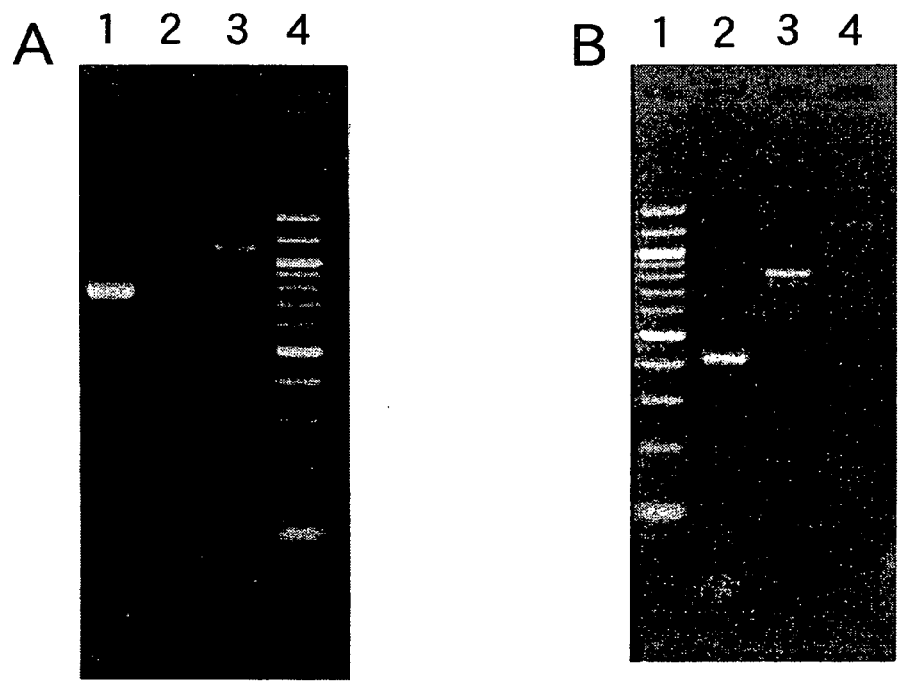
FIG. 4(A) shows an electrophoretic gel where 4 μl of fraction E/B target DNA treated with Sse8387I were subjected to a PCR so that each gene was amplified and 10 μl were subjected to a 3% agarose gel electrophoresis at 100 volts for 40 minutes by a conventional manner and stained with ethidium bromide. Lane 1: *Escherichia coli* gene; lane 2: *Bacillus pumilus* gene; lane 3: yeast gene (for reference); lane 4: size marker DNA (100, 200, 300, 400, 500, 600, 700, 800, 900, 1000, 1200 and 1500 base pairs from bottom; the same hereinafter as well).
FIG. 4(B) shows an electrophoretic gel where 4 μl of fraction H/E/B target DNA treated with Sse8387I were subjected to a PCR so that each gene was amplified and 10 μl were subjected to a 3% agarose gel electrophoresis at 100 volts for 40 minutes by a conventional manner and stained with ethidium bromide. Lane 1: size marker DNA; lane 2: human gene; lane 3: *Escherichia coli* gene; and lane 4: *Bacillus pumilus* gene.
Figure 5:
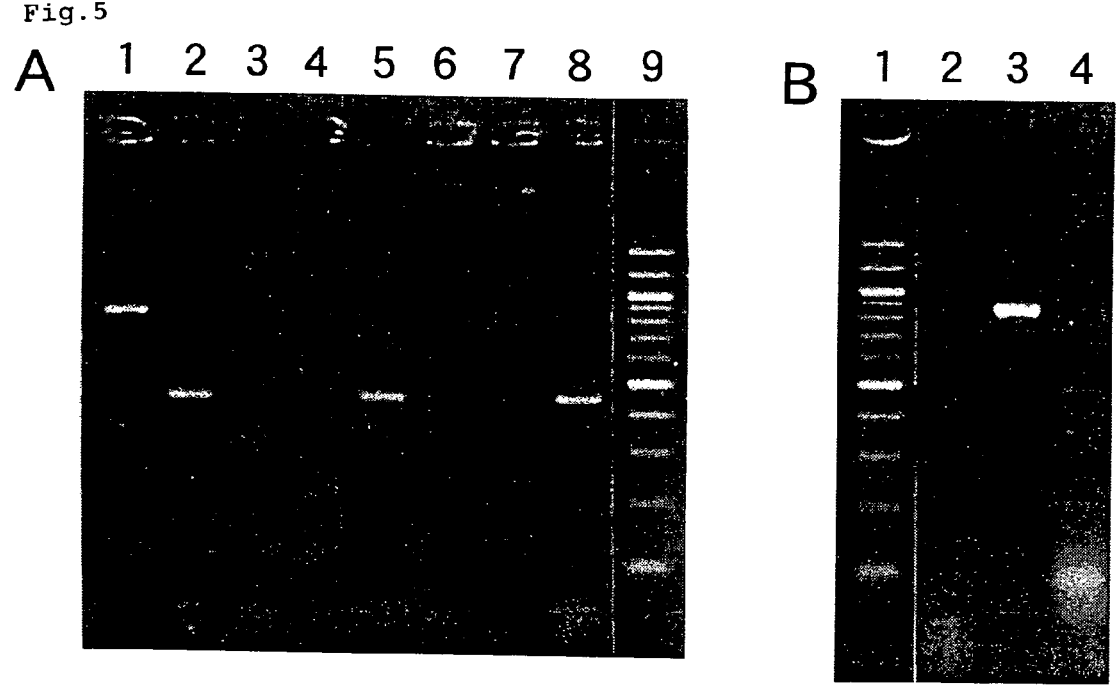
FIG. 5(A) shows an electrophoretic gel where nucleic acid which was treated with alkali and precipitated with ethanol was dissolved in 18 μl of water and 1 μl of TE, then 10×PCR buffer, Bx10, dNTP, rTaq and primer set were added to prepare 25 μl of reaction solution, a PCR was carried out therefor and a part of the reaction solution was subjected to a 3% agarose gel electrophoresis at 100 volts for 40 minutes by a conventional manner and stained with ethidium bromide. A part of the reaction solution (3 μl) was used for the lanes 1, 2, 4, 5, 7 and 8 while, for the lanes 3 and 6, a part of the reaction solution (9 μl) was used. Lane 1: 1° *Escherichia coli* gene; lane 2: 1° *Bacillus pumilus* gene; lane 3: 2° *Escherichia coli* gene; lane 4: 2° *Escherichia coli* gene; lane 5: 2° *Bacillus pumilus* gene; lane 6: 3° *Escherichia coli* gene; lane 7: 3° *Escherichia coli* gene; lane 8: 3° *Bacillus pumilus* gene; and lane 9: size marker DNA.
FIG. 5(B) shows an electrophoretic gel where nucleic acid which was treated with alkali and precipitated with ethanol was dissolved in 18 μl of water and 1 μl of TE, then 10×PCR buffer, Bx10, dNTP, rTaq and primer set were added to prepare 25 μl of reaction solution, a PCR was carried out therefor and an aliquot of the reaction solution in an equivalent amount was subjected to a 3% agarose gel electrophoresis at 100 volts for 40 minutes by a conventional manner and stained with ethidium bromide. Lane 1: size marker DNA; lane 2: 3° human gene; lane 3: 3° *Escherichia coli* gene; lane 4: 3° *Bacillus pumilus* gene.

As shown in FIG. 4A, bands of PCR products of *Escherichia coli* gene and *Bacillus pumilus* gene of E/B DNA mixed solution well reflected the amount of each DNA. When it was subjected to one hybridization (1°), *Escherichia coli* gene and *Bacillus pumilus* gene became nearly the same amount. When it was further subjected to that twice (2°) and thrice (3°), the result was that *Escherichia coli* gene<<*Bacillus pumilus* gene (FIG. 5A). Thus, *Escherichia coli* gene which occupied most of the mixture was removed predominantly. This showed that the relative degree of concentration was far more than 10,000-fold.

As will be noted from FIG. 4B, bands of PCR products of human gene, *Escherichia coli* gene and *Bacillus pumilus* gene in an H/E/N DNA mixture well reflected the amount of each DNA. Since the gene of *Bacillus pumilus* exsits only in a very small amount in a DNA mixture, there are many non-specific bands as compared with the case where only *Bacillus pumilus* DNA was present in quite a small amount and a band for the specific band for 430 base pairs was noted slightly. When this was subjected to hybridization for three times (3°), it was noted that *Escherichia coli* gene was significantly concentrated as compared with human gene (FIG. 5B). Since human gene was about one-several tenth and *Escherichia coli* gene was 5- to 10-fold as compared with the case of control PCR (FIG. 4B), degree of concentration was calculated to be about several hundred times. In the case of *Bacillus pumilus* gene, non-specific bands disappeared and specific bands were able to be clearly identified as well and, as compared with the contaminated DNA, it was noted that a significant concentration was achieved. At that time, the concentration was not so significant as compared with *Escherichia coli* gene and that can be interpreted to support the fact that the human DNA which was excessively present at first was specifically removed.

Example 2

As a minor microbe, *Sulfolobus shibatae* which was a thermophilic and acidophilic bacterium was selected, DNA of *S. shibatae* and DNA of *Escherichia coli* were mixed and the same experiment as in Example 1 was carried out whereupon it was confirmed that, as a result of a selective removal of *Escherichia coli* DNA, the DNA of *S. shibatae* which was present only one-thousandth of *E. coli* DNA was relatively concentrated. DNA of *S. shibatae* was prepared from the microbe using Gen Torukun (trade name; manufactured by Takara Shuzo).

In Example 2, the same restriction enzyme, buffer, reagent, etc. as in Example 1 were used and, with regard to the things which were not mentioned in Example 1, the followings were used.
(a) 10×Mirus Labeling Buffer A (Mirus): 200 mM MOPS, pH 7.5
(b) Glycogen: 20 mg/ml
(c) MAGNOTEX-SA (Takara Shuzo): Hybridized DNA was removed using a MAGNOTEX-SA kit by a method mentioned in the manual of the kit. Thus, MAGNOTEX-SA (50 µl; 1 mg) was placed in a 1.5 ml-tube, the tube was allowed to stand for 1 minute on a magnetic stand and the supernatant liquid was removed. A 2×Binding Buffer attached to the kit which was in the same amount as the biotin-labeled DNA solution was mixed, added to the tube, mixed and allowed to stand at room temperature for 10 minutes. The tube was allowed to stand for 1 minute on the magnetic stand and the supernatant liquid was recovered. Additional 200 µl of 1×Binding Buffer were added to the MAGNOTEX-SA and washed, and the washing was repeated once again. After mixing, the tube was allowed to stand for 1 minute on the magnetic stand and then the supernatant liquid was recovered.

[Operation 1. Preparation of DNA mixed solution]

*E. coli* DNA (80 µg) and 80 ng of *S. shibatae* DNA were dissolved in 440 µl of TE to prepare a liquid A.

[Operation 2. Preparation of driver DNA (fragmentation and biotination of DNA)]

To the liquid A containing 75 µg of *E. coli* DNA and 75 ng of *S. shibatae* DNA were added 120 µl of 10×B, 600 units of MspI and water to make 1.2 ml, and the mixture was kept at 37° C. for 2 hours to cleave the DNA and then treated at 60° C. for 15 minutes to inactivate the MspI. The reaction solution was divided into three equal parts and the DNA fragment was precipitated with ethanol and recovered by a centrifugal separator (hereinafter, this will be referred to as E/S mix DNA fragment).

The precipitate in each test tube (containing ⅓ equivalent of E/S mix DNA fragment) was dissolved in 200 µl of water and 25 µl of 10×Mirus Labeling Buffer A, then 25 µl of Mirus Label IT reagent were added and the reaction was carried out at 37° C. for 2 hours to label the DNA with biotin. To this were added 25 µl of 5M NaCl and 550 µl of ethanol and the mixture was stored at −20° C.

[Operation 3. Preparation of target DNA (partial hydrolysis of DNA)]

To the liquid A containing 2.5 µg of *S. shibatae*DNA were added 10 µl of 10×M, 10 µl of 0.1% BSA, 20.4 units of Sse8387I and water to make 100 µl, the mixture was kept at 37° C. for 2 hours to cleave the DNA and then treated at 60° C. for 15 minutes to inactive the Sse8387I. To this were added 10 µg of NaOAc, 220 µl of ethanol and 1 µl of glycogen followed by stirring at −20° C. (hereinafter, this will be referred to as E/S target DNA fragment).

[Operation 4. Hybridization]

A test tube containing the ethanol-precipitated E/S target DNA was subjected to centrifugation of 15000 rpm for 20 minutes and the supernatant liquid was discarded. To the same test tube were added 400 µl of a suspension of the ethanol-precipitated E/S driver DNA and subjected to centrifugation of 15000 rpm for 20 minutes. The supernatant liquid was discarded, additional 425 µl of suspension of ethanol-precipitated E/S driver DNA were added, the mixture was centrifuged and the supernatant liquid was discarded. The finally obtained precipitate was dissolved in 9.28 µl of water and 0.96 µl of 3N NaOH at room temperature, quickly cooled on ice, then 0.96 µl of 3N HCl and 50 mM Tris-HCl (pH 7.2)

were added thereto, then 8 µl of 20×SSC and 20.8 µl of formamide were added thereto and well mixed therewith and the mixture was called 0°. One drop of mineral oil was dropped thereinto, the mixture was tightly closed with a cover and warmed at 37° C. to carry out a hybridization reaction. After 24 hours, 10 µl of the hybridization reaction solution were taken out and the biotin-labeled DNA was removed using 1 mg of MAGNOTEX-SA. To the recovered supernatant liquid were added 20 µl of NaOAc, 500 µl of ethanol of −20° C. and 1 µl of glycogen, and a precipitate was obtained by centrifugation of 15000 rpm for 15 minutes and named 1°.

Removal of biotin-labeled DNA using 1 mg MAGNOTEX-SA was also carried out for each of 10 µl (2°) and 20 µl (3°) of the remaining hybridization reaction solution as well. To the recovered supernatant liquid were added 20 µl of NaOAc, 500 µl of ethanol of −20° C. and 1 µl of glycogen and subjected to a centrifugation of 15000 rpm for 15 minutes to give a precipitate (2° precipitate: A; 3° precipitate: B). On the other hand, ⅓ equivalent (2°) and one tube (3°) of the driver DNA were centrifuged under the same condition, the precipitate was separated and dissolved in 80 µl water+10 µl of 3N NaOH and each of A and B was dissolved in all amount thereof. After addition of 15 µl of 3N HCl+50 mM Tris-HCl (pH 7.2) thereto, 300 µl of ethanol of −20° C. were added thereto and mixed therewith and the mixture was allowed to stand in a freezer of −80° C. for 30 minutes or longer. The precipitate prepared by the centrifugation was well dissolved in 4.64 µl water+0.48 µl of 3N NaOH at room temperature and quickly cooled on ice, 0.48 µl of 3N HCl+50 mM Tris-HCl (pH 7.2), 4 µl of 20×SSC and 10.4 µl of formamide were added thereto successively, then one drop of mineral oil was layered and the mixture was kept at 37° C. After 24 hours, 10 µl of the hybridization reaction solution were taken out from the test tube A and the target DNA was recovered by the procedure as same as above and named 2°.

With regard to B, the precipitate was obtained (3° precipitate: C) by means of removal of biotin-labeled DNA, recovery of the supernatant fluid and centrifugation at 15000 rpm for 15 minutes by the same manner as above. The driver DNA (⅓ equivalent) was centrifuged and the precipitate was separated and dissolved in 50 µl water+10 µl of 3N NaOH and C was dissolved in all amount of the above. After addition of 10 µl of 3N HCl+50 mM Tris (pH 7.2), 300 µl of ethanol of −20° C. were added thereto and mixed therewith and the mixture was allowed to stand in a freezer of −80° C. for 50 minutes or longer. The precipitate prepared by the centrifugation was well dissolved in 4.64 µl water+0.48 µl of 3N NaOH at room temperature and quickly cooled on ice, 0.48 µl of 3N HCl+50 mM of Tris-HCl (pH 7.2), 4 µl of 20×SSC and 10.4 µl of formamide were added thereto successively and one mineral oil was layered and the mixture was kept at 37° C. After 24 hours, 10 µl of the hybridization reaction solution were taken out from the test tube C and the target DNA was recovered by the same process to give 3°. Finally, all of the recovered DNA precipitate was dissolved in 50 µl of 1×TE.

Test Example 1

Checking the gene in DNA fractions

A solution for PCR (25 µl) (comprising 2.5 µl of 10×PCR Buffer, 2 µl of dNTP, 0.25 µl of rTaq, 1 µl of a primer set, 3 µl of template DNA being added with water to make 25 µl) was prepared and PCR of 94° C./1 minute, 60° C./1 minute and 72° C./2 minutes was carried out for 35 cycles using a Thermal Cycler (Takara Shuzo) followed by allowing to stand at 72° C. for 8 minutes and cooling down to 4° C. With regard to the primer set, each 0.5 µl of Ef and Er (for *E. coli* gene) and Sf and Sr (for *S. shibatae* gene) were used.

Each of the following oligonucleotides was dissolved in TE to prepare a 100 µM solution and that was used as the above-mentioned primer.

(a) *Escherichia coli*: The following parts of ompA gene (ecompa.gb_bal) were used as primers.

```
Ef2  5'-TCCGAAAGATAACACCTG-3'   (SEQ ID NO: 7)
Er2  5'-GGGATACCTTTGGAGAT-3'    (SEQ ID NO: 8)
```

Amplified product by the PCR had 807 base pairs.

(b) *S. shibatae*: The following parts of esterase gene (EstI) were used as primers.

```
Sf  5'-ATGCCCCTAGATCCTCGAATC-3'   (SEQ ID NO: 9)
Sr  5'-TCAACTTTTATCATAAAATGTACG-3' (SEQ ID NO: 10)
```

Amplified product by the PCR had 918 base pairs.

With regard to other solutions, the followings were used.
(i) 10×PCR Buffer: 100 mM Tris-HCl (pH 8.3)+500 mM KCl+15 mM MgCl$_2$
(ii) dNTP mix: each 2.5 mM of dATP+dGTP+dCTP+dTTP
(iii) Taq: 5 units/µl (solvent: 20 mM Tris-HCl+100 mM KCl+0.1 mM EDTA+1 mM DTT+0.5% Tween 20+0.5% Nonidet P-40+50% glycerol)
(iv) DNA template Test Example 2

Quantitative determination by means of a real-time PCR

In order to analyze the existing ratio of various genes in a DNA mixture, mode of amplification of the sample was analyzed for each cycle by means of a real-time PCR method. Since it was not possible to analyze the existing ratio for each gene by the above-mentioned PCR method, a Light Cycler quick system 330 (manufactured by Roche Diagnostics) was used for the analysis of existing ratio of *E. coli* gene and *S. shibatae* gene.

Composition of the reaction solution for PCR was composed of 5 µl of template DNA, 2 µl of Light Cycler-DNA master SYBR Green I, 1 µl of primer set and 1.6 µl of 25 mM MgCl$_2$ (final concentration: 3 mM) where water was added to make 20 µl.

Each of the following oligonucleotides was dissolved in TE and the resulting 10 µM solution was used as the above-mentioned primers.

(a) *E. coli*: The following parts of ompA gene (ecompa.gb_bal) were used as primers.

```
Ef2  5'-TCCGAAAGATAACACCTG-3'   (SEQ ID NO: 7)
Er2  5'-GGGATACCTTTGGAGAT-3'    (SEQ ID NO: 8)
```

Amplified product by PCR had 807 base pairs.

(b) *S. shibatae*: The following parts of esterase gene (EstI) were used as primers.

```
Sf  5'-ATGCCCCTAGATCCTCGAATC-3'   (SEQ ID NO: 9)
Sr  5'-TCAACTTTTATCATAAAATGTACG-3' (SEQ ID NO: 10)
```

Amplified product by PCR had 918 base pairs.

[Result 2]

Figure 7:
FIG. 7 shows the result of Test Example 1 of Example 2. Each gene was amplified by target DNA (0°), 1°, 2° and 3° by a PCR. It (8 μl) was subjected to electrophoresis at 100 V for 30 minutes using 0.8% agarose (manufactured by K. K. Nippon Gene) and stained with ethidium bromide. As to a size marker, λ-Hind III digest was used. Lane 1: size marker DNA (λ-Hind III); lane 2: $0^0$ *Escherichia coli* gene; lane 3: $0^0$ *S. shibatae* gene; lane 4: $2^0$ *Escherichia coli* gene; lane 5: $1^0$ *S. shibatae* gene; lane 6: $2^0$ *Escherichia coli* gene; lane 7: $2^0$ *S. shibatae* gene; lane 8: $3^0$ *Escherichia coli* gene; lane 9: $3^0$ *S. shibatae* gene; lane 10: reaction solution of PCR containing no template DNA of *Escherichia coli*; and lane 11: reaction solution of PCR containing no template DNA of *S. shibatae*.

As shown in FIG. 7, it was noted that the band of *E. coli* gradually decreased as it was concentrated and, at 3°, a complete removal was achieved. On the other hand, it was confirmed that *S. shibatae* gene was nearly in the same amount throughout a series of steps (incidentally, the band of low-molecular side was believed that the primer became a dimer). The reason why the non-specific bands were many as a whole was believed to be the fact that the target DNA was partially digested by Sau3A1.

In an amplification curve for *E. coli* DNA, an exponential growth phase was observed at 18.2 cycles, 20.74 cycles, 23.31 cycles and 23.80 cycles in the case of the target DNA, 1° DNA, 2° DNA and 3° DNA, respectively, and it was noted from the above that copy numbers were largest for the target DNA decreasing in the order of 1°, 2° and 3° whereby *E coli* DNA occupying the most part was removed predominantly.

On the other hand, in an amplification curve for *S. shibatae* DNA, they were 19.22 cycles for target DNA and 1° DNA, 20.58 cycles for 2° DNA and 20.65 cycles for 3° DNA and, although a decrease was noted in 1°→2°, the existing ratio rarely changed even after a series of concentrating steps as compared with the reducing rate of *E. coli*. Further, as a result of two hybridizations, *E. coli* DNA and *S. shibatae* DNA became in nearly the same amount and, as a result of three hybridizations, the outcome was *E. coli* DNA<<*S. shibatae* DNA. From the above results, it was quantitatively confirmed that, when the existing ratio of each gene in a DNA mixed solution was analyzed using a real-time PCR method, *E. coli* DNA shown in the result by electrophoresis of FIG. 7 was selectively removed.

Industrial Applicability

It is now possible to concentrate the rare gene in a DNA sample to such an extent that it becomes more than abundant gene when a method for the concentration of rare gene, a kit for the concentration of rare gene or an apparatus for the concentration of the rare gene according to the present invention is used. In addition, it is not necessary that the abundant gene which is to be removed from the DNA sample is a known one. Accordingly, there is an advantage that, for example, DNA or the like extracted from specimens from the natural world such as soil, lake water or river water can be used as a sample.

As such, when the rare gene is concentrated, it is possible to greatly decrease the total clone numbers of a gene library to be screened for cloning the said gene. As a result, significant reduction is possible in terms of human labor, cost and time. Accordingly, useful gene such as gene of enzymes which are important in view of chemical industry or synthetic gene group of antibiotics and lead compounds for pharmaceutical and agricultural chemicals can be obtained more easily and quickly than in the conventional methods. Besides the above, it is also possible that gene of cell surface antigen is obtained using a method for the concentration of rare gene according to the present invention and an antibody is prepared using the said gene or gene information whereupon cell or microbe having an antigen therefor is identified or the said cell or microbe is isolated using a cell sorter such as FACS. It is further possible that a new gene is obtained by analyzing the base sequence of the total genome of such an isolated cell or microbe. It is furthermore possible that the gene of microbe parasitizing or infecting the animals or plants including human being is concentrated by the method or the apparatus according to the present invention whereupon the parasitizing or infecting microbe is identified, and it is still further possible that the function of the said gene is clarified and duly utilized. As such, various applications are possible.

The invention claimed is:

1. A method for the concentration of a gene, which is present in a small amount, from a DNA sample containing the gene present in a small amount and a gene, which is present in a large amount, wherein said DNA sample is prepared from a specimen where at least two kinds of microbes, organism tissues or cells are mixed, and obtained from nature, and said DNA sample is subjected to the following method to separate the gene present in a small amount from the gene present in a large amount, said method comprising:
   (a) dividing the DNA sample into two equal parts, one part being called a driver DNA fraction while the other part is called a target DNA fraction;
   (b) cleaving DNA in each of the driver DNA fraction and the target DNA fraction, such that the molecular weight of the driver DNA is made lower than the molecular weight of the target DNA, so that the average chain length of the driver DNA is 200~300 base pairs and the average chain length of the target DNA is 1000 or more base pairs, further wherein the cleavage of DNA for the driver DNA fraction is performed with a four-base recognizing restriction enzyme and the cleavage of DNA for the target DNA fraction is performed with a 5-8 base recognizing restriction enzyme;
   (c) labeling the driver DNA;
   (d) mixing the target DNA with an excessive amount of the labeled driver DNA, then treating the DNA in the mixed solution to make the DNA single-stranded and then hybridizing the DNA;
   (e) by means of the labeling of the driver DNA, removing a double-stranded DNA formed by the driver DNA and the target DNA from the above mixed solution; and
   (f) carrying out the operations of (d) and (e) one or more times, where, instead of the target DNA, there is used a DNA solution obtained in (e) wherefrom the double-stranded DNA is removed.

2. The method for the concentration of a gene, which is present in a small amount according to claim 1, wherein the ratio (d/t) of the mixed amount (d) of the driver DNA to the mixed amount (t) of the target DNA is more than 1 and up to 1,000.

3. The method for the concentration of a gene, which is present in small amount according to claim 1, wherein the driver DNA is labeled with biotin, digoxin, fluorescein or rhodamine.

4. A method for the concentration of a gene, which is present in a small amount, from a DNA sample containing the gene present in a small amount and a gene, which is present in a large amount, wherein said DNA sample is prepared from a specimen where at least two kinds of microbes, organism tissues or cells are mixed, and obtained from nature, and said DNA sample is subjected to the following method to separate the gene present in a small amount from the gene present in a large amount, said method comprising:
   (a) dividing the DNA sample into two equal parts, one part being called a driver DNA fraction while the other part is called a target DNA fraction;
   (b) cleaving DNA in each of the driver DNA fraction and the target DNA fraction by ultrasonic wave or mechanical shearing force so that the molecular weight of the driver DNA is made lower than the molecular weight of the target DNA;
   (c) labeling the driver DNA;
   (d) mixing the target DNA with an excessive amount of the driver DNA, then treating the DNA in the mixed solution to make the DNA single-stranded and then hybridizing the DNA;
   (e) by means of the labeling of the driver DNA, removing a double-stranded DNA formed by the driver DNA and the target DNA from the above mixed solution; and
   (f) carrying out the operations of (d) and (e) two or more times, where, instead of the target DNA, there is used a DNA solution obtained in (e) wherefrom the double-stranded DNA is removed.

5. A method for the concentration of a gene, which is present in a small amount, from a DNA sample containing the gene present in a small amount and a gene, which is present in a large amount, wherein said DNA sample is prepared from a specimen where at least two kinds of microbes, organism tissues or cells are mixed, and obtained from nature, and said DNA sample is subjected to the following method to separate the gene present in a small amount from the gene present in a large amount, said method comprising:
   (a) dividing the DNA sample into two equal parts, one part being called a driver DNA fraction while the other part is called a target DNA fraction;
   (b) cleaving DNA in each of the driver DNA fraction and the target DNA fraction , at which time, the molecular weight of the driver DNA is made lower than that of the target DNA, so that the average chain length of the driver DNA is 200~300 base pairs and the average chain length of the target DNA is 1000 or more base pairs, wherein the cleavage of DNA for the driver DNA fraction is performed with a four-base recognizing restriction enzyme and the cleavage of DNA for the target DNA fraction is performed with 5-8 base recognizing restriction enzyme;
   (c) treating the driver DNA fraction and the target DNA fraction to make the DNA single stranded;
   (d) fixing the driver DNA which is made single-stranded on a carrier;
   (e) contacting or mixing the carrier where the single-stranded driver DNA is fixed with a solution of the target DNA made single-stranded to perform hybridization;
   (f) separating the carrier and the solution and removing the target DNA forming a double-strand with the driver DNA; and
   (g) carrying out the operations of (e) and (f) one or more times using a target DNA solution obtained in (f) instead of the target DNA solution obtained in (b).

6. A method for the analysis of a rare gene which comprises a step of concentrating a small amount of the rare gene by the method according to claim 1 or 5, a step of obtaining the rare gene from the resulting DNA sample where the rare gene is concentrated and a step of analyzing the base sequence of the rare gene.

7. The method for the concentration of a gene, which is present in small amount according to claim 5, wherein the four-base recognizing restriction enzyme is MspI and the 5-8 recognizing restriction enzyme is Sse8387I.

8. A method for the concentration of a gene, which is present in a small amount, from a DNA sample containing the gene present in a small amount and a gene, which is present in a large amount, wherein said DNA sample is prepared from a specimen where at least two kinds of microbes, organism tissues or cells are mixed, and obtained from nature, and said DNA sample is subjected to the following method to separate the gene present in a small amount from the gene present in a large amount, said method comprising:
   (a) dividing the DNA sample into two equal parts, one part being called a driver DNA fraction while the other part is called a target DNA fraction;
   (b) cleaving DNA in each of the driver DNA fraction and the target DNA fraction by a restriction enzyme so that the molecular weight of the driver DNA is made lower than the molecular weight of the target DNA;
   (c) labeling the driver DNA;
   (d) mixing the target DNA with an excessive amount of the driver DNA, then treating the DNA in the mixed solution to make the DNA single-stranded and then hybridizing the DNA;
   (e) by means of the labeling of the driver DNA, removing a double-stranded DNA formed by the driver DNA and the target DNA from the above mixed solution; and
   (f) carrying out the operations of (d) and (e) two or more times, where, instead of the target DNA, there is used a DNA solution obtained in (e) wherefrom the double-stranded DNA is removed.

9. The method for the concentration of a gene, which is present in a small amount according to claim 8,
   wherein the cleavage of DNA for the driver DNA fraction is carried out by a four-base recognizing restriction enzyme and the cleavage of DNA for the target DNA fraction is carried out by a 5-8 base recognizing restriction enzyme.

10. The method for the concentration of a gene, which is present in a small amount according to claim 9, wherein the cleavage of DNA in step (b) is carried out so that the average chain length of the target DNA is 1000 or more base pairs, wherein the four-base recognizing restriction enzyme is MspI and the 5-8 base recognizing restriction enzyme is Sse8387I.

* * * * *